United States Patent [19]
Au-Young et al.

[11] Patent Number: 5,969,104
[45] Date of Patent: Oct. 19, 1999

[54] HUMAN C-TYPE LECTIN

[75] Inventors: Janice Au-Young, Berkeley; Benjamin Graeme Cocks, Palo Alto; Surya K. Goli, Sunnyvale; Jennifer L. Hillman, San Jose, all of Calif.

[73] Assignee: Incyte Pharmaceuticals, Inc., Palo Alto, Calif.

[21] Appl. No.: 09/113,788

[22] Filed: Jul. 10, 1998

Related U.S. Application Data

[62] Division of application No. 08/688,342, Jul. 30, 1996.

[51] Int. Cl.$^6$ .................................................... C07K 14/00
[52] U.S. Cl. ............................................ 530/350; 530/380
[58] Field of Search ...................................... 530/350, 380

[56] References Cited

PUBLICATIONS

Masaki et al. (1994) GenBank Database, Accession No. R99588.
Sawamura et al. (1997) Nature 386:73–77.
Spiess, M., "The Asialoglycoprotein Receptor: A Model for Endocytic Transport Receptors," *Biochem.* 29 (43):10009–10018 (Oct. 30, 1990).
Fallon, R.J., "Tyrosine Phosphorylation of the Asialoglycoprotein Receptor" *Biol. Chem.* 265:3401–3406 (1990).
Athamna, A. et al., "Lectinophagocytosis of Encapsulated *Klebsiella pneumoniae* Mediated by Surface Lectins of Guinea Pig Alveolar Macrophages and Human Monocyte–Derived Macrophages" *Infect. Immun.* 59:1673–1682 (1991).
Suzuki, N. et al., "Molecular Cloning and Expression of cDNA Encoding Human Macrophage C–Type Lectin" *J. Immunol.* 156:128–135 (1996).
Oda, S. et al., "Binding of Activated Macrophages to Tumor Cells through a Macrophage Lectin and Its Role in Macrophage Tumoricidal Activity" *J. Biochem (Tokyo)* 105:1040–1043 (1989).
Imai, Y. et al., "Quantitative measurement of carbohydrate binding activity of mouse macrophage lectin" *J. Immunol Methods* 171:23–31 (1994).
Russell, M.E. et al., "Identification and Upregulation of Galactose/N–acetylgalactosamine Macrophage Lectin in Rat Cardiac Allografts with Arteriosclerosis" *J. Clin. Invest.* 94:722–730 (1994).
Goswami, S. et al., "Mycotin: a lectin involved in the adherence of Mycobacteria to macrophages" *FEBS Lett.* 355:183–186 (1994).
Chang, C., et al., "Molecular characterization of human CD94: a type II membrane glycoprotein related to the C–type lectin superfamily" *Eur. J. Immunol.* 25:2433–2437 (1995).

*Primary Examiner*—Robert A. Wax
*Assistant Examiner*—Enrique D. Longton
*Attorney, Agent, or Firm*—Incyte Pharmaceuticals, Inc.

[57] ABSTRACT

The present invention provides a polynucleotide (mctl) which identifies and encodes a novel human C-type lectin (MCTL). The invention provides for genetically engineered expression vectors and host cells comprising the nucleic acid sequence encoding MCTL. The invention also provides for the use of substantially purified MCTL and its agonists in the commercial production of recombinant proteins and in pharmaceutical compositions for the treatment of diseases associated with the expression of MCTL. Additionally, the invention provides for the use of antisense molecules to mctl in pharmaceutical compositions for treatment of diseases associated with the expression of MCTL. The invention also describes diagnostic assays which utilize diagnostic compositions comprising the polynucleotide, fragments or the complement thereof, which hybridize with the genomic sequence or the transcript of mctl. The present invention also relates to anti-MCTL antibodies which specifically bind to MCTL.

2 Claims, 4 Drawing Sheets

```
              9            18           27           36           45           54
5' CA CAG ACA GTC ATC TCA GGG GCA GAA AGA AAA GAG CTC CCA AAT GCT ATA TCT 63           72           81           90           99          108
   ATT CAG GGG CTC TCA AGA ACA ATG GAA TAT CAT CCT GAT TTA GAA AAT TTG GAT
                                 M   E   Y   H   P   D   L   E   N   L   D 117          126          135          144          153          162
   GAA GAT GGA TAT ACT CAA TTA CAT TTC GAC TCT CAA AGC AAT ACC AGG ATA GCT
    E   D   G   Y   T   Q   L   H   F   D   S   Q   S   N   T   R   I   A 171          180          189          198          207          216
   GTT GTT TCA GAG AAA GGA TCG TGT GCT GCA TCT CCT CCT TGG CGC CTC ATT GCT
    V   V   S   E   K   G   S   C   A   A   S   P   P   W   R   L   I   A 225          234          243          252          261          270
   GTA ATT TTG GGA ATC CTA TGC TTG GTA ATA CTG GTG GTA GCT GTG GTC CTG GGT
    V   I   L   G   I   L   C   L   V   I   L   V   V   A   V   V   L   G 279          288          297          306          315          324
   ACC ATG GGG GTT CTT TCC AGC CCT TGT CCT CCT AAT TGG ATT ATA TAT GAG AAG
    T   M   G   V   L   S   S   P   C   P   P   N   W   I   I   Y   E   K 333          342          351          360          369          378
   AGC TGT TAT CTA TTC AGC ATG TCA CTA AAT TCC TGG GAT GGA AGT AAA AGA CAA
    S   C   Y   L   F   S   M   S   L   N   S   W   D   G   S   K   R   Q 387          396          405          414          423          432
   TGC TGG CAA CTG GGC TCT AAT CTC CTA AAG ATA GAC AGC TCA AAT GAA TTG GGA
    C   W   Q   L   G   S   N   L   L   K   I   D   S   S   N   E   L   G 441          450          459          468          477          486
   TTT ATA GTA AAA CAA GTG TCT TCC CAA CCT GAT AAT TCA TTT TGG ATA GGC CTT
    F   I   V   K   Q   V   S   S   Q   P   D   N   S   F   W   I   G   L 495          504          513          522          531          540
   TCT CGG CCC CAG ACT GAG GTA CCA TGG CTC TGG GAG GAT GGA TCA ACA TTC TCT
    S   R   P   Q   T   E   V   P   W   L   W   E   D   G   S   T   F   S 549          558          567          576          585          594
   TCT AAC TTA TTT CAG ATC AGA ACC ACA GCT ACC CAA GAA AAC CCA TCT CCA AAT
    S   N   L   F   Q   I   R   T   T   A   T   Q   E   N   P   S   P   N 603          612          621          630          639          648
   TGT GTA TGG ATT CAC GTG TCA GTC ATT TAT GAC CAA CTG TGT AGT GTG CCC TCA
    C   V   W   I   H   V   S   V   I   Y   D   Q   L   C   S   V   P   S
```

FIGURE 1A

```
                  657           666           675           684           693           702
TAT AGT ATT TGT GAG AAG AAG TTT TCA ATG TAA GGG GAA GGG TGG AAG AAG GAG
 Y   S   I   C   E   K   K   F   S   M   *

711           720           729           738           747           756
AGA RAN AAT ATG TGA GGT AKT AAG GAG GAC AGA AAA NCA GAA CMG AAA AGA KTW 765           774           783           792           801           810
ACA GCT GAA GGT CAA GAT AAA TGC AGA AAA NTG TTT ARA RAG CTT KGC CAA CTG 819           828           837           846           855           864
TWA TCT TAA CCM ARR AAT TGA AGG GAG ARG CTG TGA TTT CTG TAT TTG TCG GCN 873           882           891           900           909           918
ACT ACA GGT AGG CTA GTA TTA TTT TTC TAG TTA GTA AAN CCC AAA NAT GGA TCA 927           936           945           954           963           972
GGG CTC CAA CNG NAT TTA ATT TTA ATA TTA TTT TNN GAA ANA GGT CCC CTT TGT 981           990
TCC CAG GTG AAT NCA TNC C 3'
```

FIGURE 1B

```
  1  M E - Y H P D L E N L D E D G Y T Q L H F D S Q S N T R I A   MCTL
  1  M A V F K T T L - - - - - - - - - - - - - - - - - - - - - -   GI 1098616
  1  M T R T Y E N F Q Y L E N K - V K V Q G F K N G P L P L Q S   GI 1235724
  1  M T K E Y Q D L Q H L D N E E S D H H Q L R K G P P P P Q P   GI 179079

30  V V S E - - K G S C A A S P P W R L I A V I L G I L C L V -   MCTL
  9  - - - - - - - - - - - - - - W R L I S G T L G I I C L S -     GI 1098616
 30  L L Q R L R S G P C H L L L S L G L G L L L L V I I C V V G   GI 1235724
 31  L L Q R L C S G P R L L L L S L G L S L L L L V V V C V I G   GI 179079

57  - - - - I L V V A V V L - - - - - G T M G - - - - - - V L S   MCTL
 23  - - - - L M A T L G I L L K N S F T K L S - - - - - I E P     GI 1098616
 60  F Q N S K F Q R D L V T L R T D F S N F T S N T V A E I Q A   GI 1235724
 61  S Q N S Q L Q E E L R G L R E T F S N F T A S T E A Q V K G   GI 179079

72  S - - - - - - - - - - - - - - - - - - - - - - - - - - - - -   MCTL
 43  A F T P G P N I E - - - - - L Q K D S D - - - - - - - - - -   GI 1098616
 90  L T S Q G S S L E E T I A S L K A E V E G F K Q E R Q A V H   GI 1235724
 91  L S T Q G N V G R K M K S L E S Q L E K Q Q K D L S E D H     GI 179079

73  - - - - - - - - - - - - - - - - - - - - - - - - - - - - - -   MCTL
 58  - - - - - - - - - - - - - - - - C - - - - - - - - - - - - -   GI 1098616
120  S E M L L R V Q Q L V Q D L K K L T C Q V A T L N N G E E     GI 1235724
121  S S L L L H V K Q F V S D L R S L S C Q M A A L Q G N G S E   GI 179079

73  - - - - - - - - P C P P N W I I Y E K S C Y L F S M S L N S W   MCTL
 59  - - - - - - C S C Q E K W V G Y R C N C Y F I S S E Q K T W   GI 1098616
150  A S T E G T C - C P V N W V E H Q D S C Y W F S H S G M S W   GI 1235724
151  R - - - - T C - C P V N W V E H E R S C Y W F S R S G K A W   GI 179079

96  D G S K R Q C W Q L G S N L L K I D S S N E L G F I V K Q V   MCTL
 83  N E S R H L C A S Q K S S L L Q L Q N T D E L D F M - - - -   GI 1098616
179  A E A E K Y C Q L K N A H L V V I N S R E E Q N F V Q K Y L   GI 1235724
176  A D A D N Y C R L E D A H L V V V T S W E E Q K F V Q H H I   GI 179079

126  S S Q P D N S F W I G L S R P Q T E V P W L W E D G S T F S   MCTL
109  - S S S Q Q F Y W I G L S Y S E E H T A W L W E N G S A L S   GI 1098616
209  G S A - - - Y T W M G L - - S D P E G A W K W V D G T D Y A   GI 1235724
206  G P V - - - N T W M G L - - H D Q N G P W K W V D G T D Y E   GI 179079

156  S N L F Q I R T T A T Q E N - - - - - - P S P N C V - W I H   MCTL
138  Q Y L F P - - - - S F E T F - - - - - - N T K N C I A Y N P   GI 1098616
234  T G F Q N W K P G Q P D D W Q G H G L G G G E D C A H F H P   GI 1235724
231  T G F K N W R P E Q P D D W Y G H G L G G G E D C A H F T D   GI 179079

179  V S V I Y D Q L C S V P S Y S I C E K K F S - - - - - - - -   MCTL
158  N G N A L D E S C E D K N R Y I C K Q Q L - - - - - - - -   GI 1098616
264  D G R W N D D V C Q R P Y H W V C E A G L G Q T S Q E S H     GI 1235724
261  D G R W N D D V C Q R P Y R W V C E T E L D K A S Q E P P L   GI 179079

201  M                                                             MCTL
179  I                                                             GI 1098616
292                                                                GI 1235724
291  L                                                             GI 179079
```

FIGURE 2

SEQUENCE LISTING (1) GENERAL INFORMATION:

(iii) NUMBER OF SEQUENCES: 5

(2) INFORMATION FOR SEQ ID NO:1:

(i) SEQUENCE CHARACTERISTICS:
      (A) LENGTH: 201 amino acids
      (B) TYPE: amino acid
      (C) STRANDEDNESS: single
      (D) TOPOLOGY: linear (ii) MOLECULE TYPE: peptide (vii) IMMEDIATE SOURCE:
      (A) LIBRARY: MMLR1DT01
      (B) CLONE: 515847

(xi) SEQUENCE DESCRIPTION: SEQ ID NO:1:

```
Met Glu Tyr His Pro Asp Leu Glu Asn Leu Asp Glu Asp Gly Tyr Thr
 1               5                  10                  15

Gln Leu His Phe Asp Ser Gln Ser Asn Thr Arg Ile Ala Val Val Ser
            20                  25                  30

Glu Lys Gly Ser Cys Ala Ala Ser Pro Pro Trp Arg Leu Ile Ala Val
        35                  40                  45

Ile Leu Gly Ile Leu Cys Leu Val Ile Leu Val Val Ala Val Val Leu
    50                  55                  60

Gly Thr Met Gly Val Leu Ser Ser Pro Cys Pro Pro Asn Trp Ile Ile
65                  70                  75                  80
```

-continued

```
            Tyr Glu Lys Ser Cys Tyr Leu Phe Ser Met Ser Leu Asn Ser Trp Asp
                         85                  90                  95

Gly Ser Lys Arg Gln Cys Trp Gln Leu Gly Ser Asn Leu Leu Lys Ile
                        100                 105                 110

Asp Ser Ser Asn Glu Leu Gly Phe Ile Val Lys Gln Val Ser Ser Gln
                        115                 120                 125

Pro Asp Asn Ser Phe Trp Ile Gly Leu Ser Arg Pro Gln Thr Glu Val
                        130                 135                 140

Pro Trp Leu Trp Glu Asp Gly Ser Thr Phe Ser Ser Asn Leu Phe Gln
            145                 150                 155                 160

Ile Arg Thr Thr Ala Thr Gln Glu Asn Pro Ser Pro Asn Cys Val Trp
                        165                 170                 175

Ile His Val Ser Val Ile Tyr Asp Gln Leu Cys Ser Val Pro Ser Tyr
                        180                 185                 190

Ser Ile Cys Glu Lys Lys Phe Ser Met
                        195                 200
```

(2) INFORMATION FOR SEQ ID NO:2:

(i) SEQUENCE CHARACTERISTICS:
        (A) LENGTH: 990 base pairs
        (B) TYPE: nucleic acid
        (C) STRANDEDNESS: single
        (D) TOPOLOGY: linear (ii) MOLECULE TYPE: cDNA (vii) IMMEDIATE SOURCE:
        (A) LIBRARY: MMLR1DT01
        (B) CLONE: 515847

(xi) SEQUENCE DESCRIPTION: SEQ ID NO:2:

```
CACAGACAGT CATCTCAGGG GCAGAAAGAA AAGAGCTCCC AAATGCTATA TCTATTCAGG      60

GGCTCTCAAG AACAATGGAA TATCATCCTG ATTTAGAAAA TTTGGATGAA GATGGATATA     120

CTCAATTACA TTTCGACTCT CAAAGCAATA CCAGGATAGC TGTTGTTTCA GAGAAAGGAT     180

CGTGTGCTGC ATCTCCTCCT TGGCGCCTCA TTGCTGTAAT TTTGGGAATC CTATGCTTGG     240

TAATACTGGT GGTAGCTGTG GTCCTGGGTA CCATGGGGGT TCTTTCCAGC CCTTGTCCTC     300

CTAATTGGAT TATATATGAG AAGAGCTGTT ATCTATTCAG CATGTCACTA AATTCCTGGG     360

ATGGAAGTAA AAGACAATGC TGGCAACTGG GCTCTAATCT CCTAAAGATA GACAGCTCAA     420

ATGAATTGGG ATTTATAGTA AAACAAGTGT CTTCCCAACC TGATAATTCA TTTTGGATAG     480

GCCTTTCTCG GCCCCAGACT GAGGTACCAT GGCTCTGGGA GGATGGATCA ACATTCTCTT     540

CTAACTTATT TCAGATCAGA ACCACAGCTA CCCAAGAAAA CCCATCTCCA AATTGTGTAT     600

GGATTCACGT GTCAGTCATT TATGACCAAC TGTGTAGTGT GCCCTCATAT AGTATTTGTG     660

AGAAGAAGTT TTCAATGTAA GGGGAAGGGT GGAAGAAGGA GAGARANAAT ATGTGAGGTA     720

KTAAGGAGGA CAGAAAANCA GAACMGAAAA GAKTWACAGC TGAAGGTCAA GATAAATGCA     780

GAAAANTGTT TARARAGCTT KGCCAACTGT WATCTTAACC MARRAATTGA AGGGAGARGC     840

TGTGATTTCT GTATTTGTCG GCNACTACAG GTAGGCTAGT ATTATTTTTC TAGTTAGTAA     900

ANCCCAAANA TGGATCAGGG CNCCAACNGN ATTTAATTTT AATATTATTT TNNGAAANAG     960

GTCCCCTTTG TTCCCAGGTG AATNCATNCC                                     990
```

(2) INFORMATION FOR SEQ ID NO:3:

(i) SEQUENCE CHARACTERISTICS:
        (A) LENGTH: 179 amino acids (B) TYPE: amino acid
            (C) STRANDEDNESS: single
            (D) TOPOLOGY: linear (ii) MOLECULE TYPE: peptide (vii) IMMEDIATE SOURCE:
            (A) LIBRARY: GenBank
            (B) CLONE: 1098616

(xi) SEQUENCE DESCRIPTION: SEQ ID NO:3:

```
Met Ala Val Phe Lys Thr Thr Leu Trp Arg Leu Ile Ser Gly Thr Leu
1               5                  10                  15

Gly Ile Ile Cys Leu Ser Leu Met Ala Thr Leu Gly Ile Leu Leu Lys
            20                  25                  30

Asn Ser Phe Thr Lys Leu Ser Ile Glu Pro Ala Phe Thr Pro Gly Pro
        35                  40                  45

Asn Ile Glu Leu Gln Lys Asp Ser Asp Cys Ser Cys Gln Glu Lys
    50                  55                  60

Trp Val Gly Tyr Arg Cys Asn Cys Tyr Phe Ile Ser Ser Glu Gln Lys
65                  70                  75                  80

Thr Trp Asn Glu Ser Arg His Leu Cys Ala Ser Gln Lys Ser Ser Leu
                85                  90                  95

Leu Gln Leu Gln Asn Thr Asp Glu Leu Asp Phe Met Ser Ser Ser Gln
            100                 105                 110

Gln Phe Tyr Trp Ile Gly Leu Ser Tyr Ser Glu Glu His Thr Ala Trp
        115                 120                 125

Leu Trp Glu Asn Gly Ser Ala Leu Ser Gln Tyr Leu Phe Pro Ser Phe
    130                 135                 140

Glu Thr Phe Asn Thr Lys Asn Cys Ile Ala Tyr Asn Pro Asn Gly Asn
145                 150                 155                 160

Ala Leu Asp Glu Ser Cys Glu Asp Lys Asn Arg Tyr Ile Cys Lys Gln
                165                 170                 175

Gln Leu Ile
```

(2) INFORMATION FOR SEQ ID NO:4:

(i) SEQUENCE CHARACTERISTICS:
            (A) LENGTH: 292 amino acids
            (B) TYPE: amino acid
            (C) STRANDEDNESS: single
            (D) TOPOLOGY: linear (ii) MOLECULE TYPE: peptide (vii) IMMEDIATE SOURCE:
            (A) LIBRARY: GenBank
            (B) CLONE: 1235724

(xi) SEQUENCE DESCRIPTION: SEQ ID NO:4:

```
Met Thr Arg Thr Tyr Glu Asn Phe Gln Tyr Leu Glu Asn Lys Val Lys
1               5                   10                  15

Val Gln Gly Phe Lys Asn Gly Pro Leu Pro Leu Gln Ser Leu Leu Gln
            20                  25                  30

Arg Leu Arg Ser Gly Pro Cys His Leu Leu Leu Ser Leu Gly Leu Gly
        35                  40                  45

Leu Leu Leu Leu Val Ile Ile Cys Val Val Gly Phe Gln Asn Ser Lys
    50                  55                  60

Phe Gln Arg Asp Leu Val Thr Leu Arg Thr Asp Phe Ser Asn Phe Thr
65                  70                  75                  80
```

```
Ser Asn Thr Val Ala Glu Ile Gln Ala Leu Thr Ser Gln Gly Ser Ser
                85                  90                  95

Leu Glu Glu Thr Ile Ala Ser Leu Lys Ala Glu Val Glu Gly Phe Lys
                100                 105                 110

Gln Glu Arg Gln Ala Val His Ser Glu Met Leu Leu Arg Val Gln Gln
            115                 120                 125

Leu Val Gln Asp Leu Lys Lys Leu Thr Cys Gln Val Ala Thr Leu Asn
130                 135                 140

Asn Asn Gly Glu Glu Ala Ser Thr Glu Gly Thr Cys Cys Pro Val Asn
145                 150                 155                 160

Trp Val Glu His Gln Asp Ser Cys Tyr Trp Phe Ser His Ser Gly Met
                165                 170                 175

Ser Trp Ala Glu Ala Glu Lys Tyr Cys Gln Leu Lys Asn Ala His Leu
                180                 185                 190

Val Val Ile Asn Ser Arg Glu Glu Gln Asn Phe Val Gln Lys Tyr Leu
            195                 200                 205

Gly Ser Ala Tyr Thr Trp Met Gly Leu Ser Asp Pro Glu Gly Ala Trp
210                 215                 220

Lys Trp Val Asp Gly Thr Asp Tyr Ala Thr Gly Phe Gln Asn Trp Lys
225                 230                 235                 240

Pro Gly Gln Pro Asp Asp Trp Gln Gly His Gly Leu Gly Gly Gly Glu
                245                 250                 255

Asp Cys Ala His Phe His Pro Asp Gly Arg Trp Asn Asp Asp Val Cys
                260                 265                 270

Gln Arg Pro Tyr His Trp Val Cys Glu Ala Gly Leu Gly Gln Thr Ser
            275                 280                 285

Gln Glu Ser His
290

(2) INFORMATION FOR SEQ ID NO:5:

(i) SEQUENCE CHARACTERISTICS:
        (A) LENGTH: 291 amino acids
        (B) TYPE: amino acid
        (C) STRANDEDNESS: single
        (D) TOPOLOGY: linear (ii) MOLECULE TYPE: peptide (vii) IMMEDIATE SOURCE:
        (A) LIBRARY: GenBank
        (B) CLONE: 179079

(xi) SEQUENCE DESCRIPTION: SEQ ID NO:5:

Met Thr Lys Glu Tyr Gln Asp Leu Gln His Leu Asp Asn Glu Glu Ser
1               5                   10                  15

Asp His His Gln Leu Arg Lys Gly Pro Pro Pro Gln Pro Leu Leu
                20                  25                  30

Gln Arg Leu Cys Ser Gly Pro Arg Leu Leu Leu Leu Ser Leu Gly Leu
            35                  40                  45

Ser Leu Leu Leu Leu Val Val Val Cys Val Ile Gly Ser Gln Asn Ser
50                  55                  60

Gln Leu Gln Glu Glu Leu Arg Gly Leu Arg Glu Thr Phe Ser Asn Phe
65                  70                  75                  80

Thr Ala Ser Thr Glu Ala Gln Val Lys Gly Leu Ser Thr Gln Gly Gly
                85                  90                  95

Asn Val Gly Arg Lys Met Lys Ser Leu Glu Ser Gln Leu Glu Lys Gln
                100                 105                 110
```

-continued

```
Gln Lys Asp Leu Ser Glu Asp His Ser Ser Leu Leu Leu His Val Lys
        115                 120                 125

Gln Phe Val Ser Asp Leu Arg Ser Leu Ser Cys Gln Met Ala Ala Leu
        130                 135                 140

Gln Gly Asn Gly Ser Glu Arg Thr Cys Cys Pro Val Asn Trp Val Glu
145                 150                 155                 160

His Glu Arg Ser Cys Tyr Trp Phe Ser Arg Ser Gly Lys Ala Trp Ala
                165                 170                 175

Asp Ala Asp Asn Tyr Cys Arg Leu Glu Asp Ala His Leu Val Val Val
                180                 185                 190

Thr Ser Trp Glu Glu Gln Lys Phe Val Gln His His Ile Gly Pro Val
        195                 200                 205

Asn Thr Trp Met Gly Leu His Asp Gln Asn Gly Pro Trp Lys Trp Val
        210                 215                 220

Asp Gly Thr Asp Tyr Glu Thr Gly Phe Lys Asn Trp Arg Pro Glu Gln
225                 230                 235                 240

Pro Asp Asp Trp Tyr Gly His Gly Leu Gly Gly Gly Glu Asp Cys Ala
                245                 250                 255

His Phe Thr Asp Asp Gly Arg Trp Asn Asp Asp Val Cys Gln Arg Pro
                260                 265                 270

Tyr Arg Trp Val Cys Glu Thr Glu Leu Asp Lys Ala Ser Gln Glu Pro
        275                 280                 285

Pro Leu Leu
        290
```

HUMAN C-TYPE LECTIN

CROSS-REFERENCE TO RELATED APPLICATIONS

This application is a divisional application of U.S. application Ser. No. 08/688,342, filed Jul 30, 1996.

FIELD OF THE INVENTION

The present invention relates to nucleic acid and amino acid sequences of a novel C-type lectin and to the use of these sequences in the diagnosis, study, prevention and treatment of disease.

BACKGROUND OF THE INVENTION

The C-type lectins are widely expressed in cells of the immune system, including macrophages, B and T lymphocytes, mast cells, and natural killer (NK) cells. The characteristic structural feature conserved among members of this family of calcium-dependent lectins is an extracellular carbohydrate recognition domain. This domain consists of a series of invariant residues arranged in a characteristic pattern (Spiess, M (1990) Biochem 29:10009–10018). Receptor proteins of the C-type lectin superfamily do not generally share significant sequence homology beyond that of the carbohydrate recognition domain. For many of these proteins, there is no direct evidence for the binding of carbohydrates, and physiological ligands have not been identified. In fact, carbohydrate-binding activity has been inferred from the homology with the carbohydrate-binding domain of the asialoglycoprotein receptor (Spiess, supra).

Many C-type lectins are classified as Type II membrane proteins. The characteristic topology of the Type II membrane protein includes an extracellular C-terminus comprising the carbohydrate binding domain, an amino terminus facing the cytosol, and a membrane-spanning domain of approximately 20 apolar residues serving as the signal for membrane insertion. Several prolines generally precede the cytoplasmic side of the transmembrane domain. The prolines are suggested to prevent the steric interference of the amino-terminal domain with the transmembrane domain during membrane insertion. The N-terminal cytosolic domains of the C-type lectins are very diverse in both length and sequence. The cytosolic domains of most endocytotic receptors contain at least one tyrosine, which may be involved in signal transduction (Spiess, supra). Phosphorylation of the cytosolic tyrosine of the asialoglycoprotein receptor, a C-type lectin, has been demonstrated (Fallon RJ (1990) J Biol Chem 265: 3401–3406). The extracellular carbohydrate binding domains are readily separated from membrane-bound C-type lectin molecules by protease treatment. These isolated, soluble domains retain structural integrity and carbohydrate binding activity, owing in part to the three intrachain disulfide bonds present in the binding domains of this class of lectin.

Many cell surface receptor molecules expressed on macrophages belong to the C-type lectin supergene family. Macrophage lectin proteins perform a variety of functions in the recognition and destruction of foreign cells and pathogens.

Serotypes of *Klebsiella pneumoniae* have been shown to bind to macrophages via the interaction of *K. pneumoniae* surface mannose residues with mannose-specific lectins on the macrophage surface. Only the *K. pneumoniae* serotypes displaying certain surface mannose polysaccharide sequences bind to, and are subsequently internalized and destroyed by macrophages (Athamna A et al (1991) Infect Immun 59: 1673–1682).

A human macrophage C-type lectin has been found to recognize Tn Ag, a well-known human carcinoma-associated epitope (Suzki N et al (1996) J Immunol 156: 128–135). Unique macrophage lectins may specifically interact with surface antigens expressed by certain abnormal or diseased cells. The lectins may direct the macrophages to abnormal or diseased cells.

Binding of activated macrophages to mastocytoma cells was inhibited by pre-incubation of the macrophages with a glycopeptide inhibitor of a Gal/GalNAc-specific macrophage C-type lectin, as well as by the addition of anti-macrophage lectin antiserum. In addition, the anti-macrophage lectin antiserum inhibited the tumoricidal activity of the activated macrophages, suggesting that the binding of activated macrophages to these tumor cells through the Gal/GalNAc-specific macrophage lectin is an important part of the tumor cell killing mechanism (Oda S et al (1989) J Biochem (Tokyo) 105: 1040–1043). Furthermore, the recombinant cytosolic carbohydrate binding domain of the mouse macrophage C-type lectin also served as an inhibitor of cytotoxic activity, indicating that the lectin was a direct mediator of the macrophage tumoricidal response (Imai Y and Irimura T (1994) J Immunol Methods 171: 23–31).

Many diseases have been identified that relate to abnormalities of macrophage function, especially adherence, chemotaxis, and microbicidal activity. Some of these abnormalities may be due to defects in the recognition of foreign particles, diseased tissues or host tissues via lectin receptor molecules expressed by the macrophages. Other conditions derive from normal, yet undesirable, functioning of macrophages. Such undesirable conditions include graft and transplant rejection and pathogen colonization of host macrophages.

Increased expression of a macrophage cell-surface lectin was localized to inflammatory cells in rat cardiac allografts. Macrophage cell-surface lectins were proposed to be linked to the chronic rejection of cardiac allografts in arteriosclerosis. In this case the lectin served as a possible mediator of macrophage infiltration (Russel ME et al (1994) J Clin Invest 94: 722–730).

Pathogenic Mycobacteria, including *M. tuberculosis*, colonize activated macrophages. The attachment of such pathogens to macrophages is the preliminary step in pathogenesis. The colonization has been shown to occur via mannose-specific lectin receptors expressed on the macrophages (Goswami S et al (1994) FEBS Lett 355: 183–186).

Macrophage lectins clearly play an important role in the recognition and destruction of diseased and non-self cells. The selective modulation of the expression and specificity of a novel macrophage lectin may allow the successful management of diseases related to macrophage function, such as graft rejection or pathogen colonization, or the exploitation of the natural cytolytic capabilities of macrophages, such as specific targeting to tumors or infected host cells.

SUMMARY OF THE INVENTION

The present invention discloses a novel human C-type lectin, MCTL, having homology to the C-type lectin superfamily of Type II membrane proteins. Accordingly, the invention features a substantially purified lectin, encoded by amino acid sequence of SEQ ID NO:1, having the characteristics of a C-type lectin.

One aspect of the invention features isolated and substantially purified polynucleotides which encode MCTL. In a particular aspect, the polynucleotide is the nucleotide sequence of SEQ ID NO:2. In addition, the invention features nucleotide sequences that hybridize under stringent conditions to SEQ ID NO:2.

A nucleic acid sequence encoding MCTL, oligonucleotides, peptide nucleic acids (PNA), fragments, portions or antisense molecules thereof, may be used in diagnostic assays of body fluids or biopsied tissues to detect expression of a nucleic acid sequence encoding MCTL. For example, a nucleic acid sequence encoding MCTL designed from SEQ ID NO:2 can be used to detect the presence of mRNA transcripts in a patient or to monitor modulation of transcripts during treatment.

The present invention relates, in part, to the inclusion of the polynucleotide encoding MCTL in an expression vector which can be used to transform host cells or organisms. Such transgenic hosts are useful for the production of MCTL. Substantially purified MCTL or fragments thereof may be useful as a pharmaceutical composition. For example, they may be used to tag the cells of tumors for cytolytic destruction.

A nucleic acid sequence encoding MCTL also provides for the design of antisense molecules useful in diminishing or eliminating expression of the genomic nucleotide sequence in conditions where MCTL activity may cause undesirable macrophage activity. For example, MCTL antisense nucleotides may be used to diminish or prevent allograft rejection.

The invention further provides diagnostic assays and kits for the detection of naturally occurring MCTL. It provides for the use of substantially purified MCTL as a positive control and to produce anti-MCTL antibodies which can be used to quantitate the amount of MCTL in human body fluids or biopsied tissues.

MCTL can be used to identify agonists which induce the production of or prolong the lifespan of the MCTL molecule or inhibitors which modulate the activity of MCTL.

The invention also relates to pharmaceutical compositions comprising MCTL, antisense molecules capable of disrupting expression of the genomic sequence encoding MCTL, and agonists, antibodies, antagonists or inhibitors of MCTL. These compositions are useful for the prevention or treatment of conditions associated with the presence or the expression of MCTL.

BRIEF DESCRIPTION OF THE FIGURES

FIGS. 1A, 1B, and 1C show the amino acid sequence (SEQ ID NO:1) and the nucleic acid sequence (SEQ ID NO:2) of the human C-type lectin MCTL, and was produced using MACDNASIS software (Hitachi Software Engineering Co Ltd).

FIGS. 2A and 2B shows the amino acid sequence alignments among MCTL (SEQ ID NO:1), human lymphocyte activation antigen CD-94 (GI 1098616; SEQ ID NO:3), human macrophage lectin 2 (GI 1235724; SEQ ID NO:4), and human asialoglycoprotein receptor H1 (GI 179079; SEQ ID NO:5) produced using the multisequence alignment program of DNASTAR software (DNAStar Inc, Madison Wis.).

DETAILED DESCRIPTION OF THE INVENTION

Definitions

Figure 3:
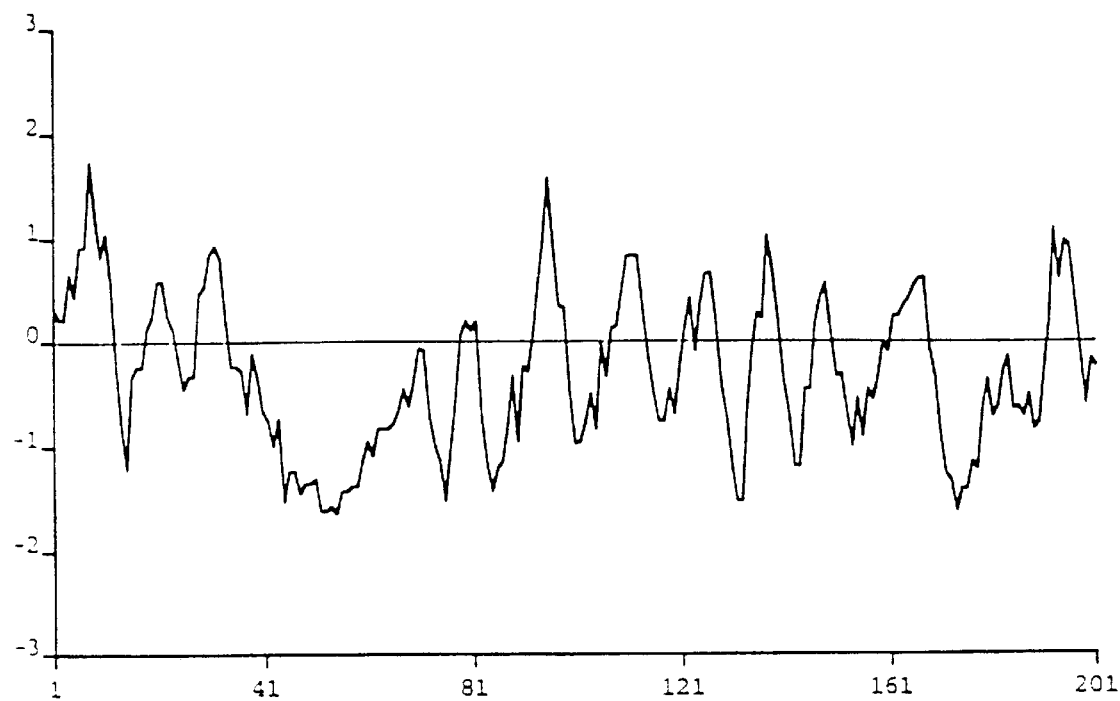
FIG. 3 shows the hydrophobicity plot (generated using MACDNASIS software) for MCTL, SEQ ID NO:1; the X axis reflects amino acid position, and the negative Y axis, hydrophobicity.

"Nucleic acid sequence" as used herein refers to an oligonucleotide, nucleotide or polynucleotide, and fragments or portions thereof, and to DNA or RNA of genomic or synthetic origin which may be single- or double-stranded, and represent the sense or antisense strand. Similarly, amino acid sequence as used herein refers to protein or peptide sequence.

"Peptide nucleic acid" as used herein refers to a molecule which comprises an oligomer to which an amino acid residue, such as lysine, and an amino group have been added. These small molecules, also designated anti-gene agents, stop transcript elongation by binding to their complementary (template) strand of nucleic acid (Nielsen PE et al (1993) Anticancer Drug Des 8:53–63).

As used herein, MCTL refers to the amino acid sequence of substantially purified MCTL obtained from any species, particularly mammalian, including bovine, ovine, porcine, murine, equine, and preferably human, from any source whether natural, synthetic, semi-synthetic or recombinant.

The present invention also encompasses MCTL variants. A preferred MCTL variant is one having at least 80% amino acid sequence similarity to the MCTL amino acid sequence (SEQ ID NO:1), a more preferred MCTL variant is one having at least 90% amino acid sequence similarity to SEQ ID NO:1 and a most preferred MCTL variant is one having at least 95% amino acid sequence similarity to SEQ ID NO:1.

A "variant" of MCTL may have an amino acid sequence that is different by one or more amino acid "substitutions". The variant may have "conservative" changes, wherein a substituted amino acid has similar structural or chemical properties, eg, replacement of leucine with isoleucine. More rarely, a variant may have "nonconservative" changes, eg, replacement of a glycine with a tryptophan. Similar minor variations may also include amino acid deletions or insertions, or both. Guidance in determining which and how many amino acid residues may be substituted, inserted or deleted without abolishing biological or immunological activity may be found using computer programs well known in the art, for example, DNASTAR software.

The term "biologically active" refers to a MCTL having structural, regulatory or biochemical functions of the naturally occurring MCTL. Likewise, "immunologically active" defines the capability of the natural, recombinant or synthetic MCTL, or any oligopeptide thereof, to induce a specific immune response in appropriate animals or cells and to bind with specific antibodies.

The term "derivative" as used herein refers to the chemical modification of a nucleic acid sequence encoding MCTL or the encoded MCTL. Illustrative of such modifications would be replacement of hydrogen by an alkyl, acyl, or amino group. A nucleic acid derivative would encode a polypeptide which retains essential biological characteristics of natural MCTL.

As used herein, the term "substantially purified" refers to molecules, either nucleic or amino acid sequences, that are removed from their natural environment, isolated or separated, and are at least 60% free, preferably 75% free, and most preferably 90% free from other components with which they are naturally associated.

Description

The present invention relates to a novel human C-type lectin, MCTL, initially identified among the partial cDNAs from a stimulated human macrophage library (MMLR1DT01) and to the use of the nucleic acid and amino acid sequences disclosed herein in the study, diagnosis, prevention and treatment of disease. Although MCTL-encoding nucleotide sequences are found transcribed in macrophages, the naturally occurring expression is not necessarily limited to macrophages.

The nucleic acid sequence encoding a portion of MCTL was first identified in the cDNA, Incyte Clone 515847, through a computer-generated search for amino acid sequence alignments. The nucleic acid sequence, SEQ ID NO:2, disclosed herein (FIGS. 1A, 1B, and 1C) and designated in lower case (mctl), encodes the amino acid sequence, SEQ ID NO:1, designated in upper case, MCTL. The present invention is based in part on the chemical and structural homology, as shown in FIGS. 2A and 2B, among MCTL and representative members of the C-type lectin superfamily including human lymphocyte activation antigen CD-94 (GI 1098616, Chang C et al (1995) Eur J Immunol 25: 2433–2437), human macrophage lectin 2 (GI 1235724, Suzuki N (1996) J Immunol 156: 128–135), and human asialoglycoprotein receptor H1 (GI 179079, Spiess M et al (1985) J Biol Chem 260: 1979–1982).

MCTL is homologous to these C-type lectins primarily within the extracellular carbohydrate binding domain (FIGS. 2A and 2B). The extracellular carbohydrate binding domain includes 6 cysteines which are strictly conserved among the C-type lectins, and inferred by homology to asialoglycoprotein receptor to form disulfides at $C_{74}$–$C_{85}$, $C102$–$C_{195}$ and $C_{174}$–$C_{187}$ in MCTL (Spiess M et al, supra). The precise alignment of these cysteine residues among the C-type lectins suggests they are important structural features of the carbohydrate binding domains. The additional residues strictly conserved in these carbohydrate binding domains are $W_{78}$, $W_{95}$, $W_{134}$, and $G_{136}$ in MCTL. From homology, the extracellular carbohydrate binding domain of MCTL is predicted to include the residues from approximately $T_{66}$ to the C-terminus at $M_{201}$.

MCTL contains a span of 21 mostly uncharged and hydrophobic amino acids from $L_{45}$ to $G_{65}$, which is predicted to form the transmembrane domain. MCTL has a predicted N-terminal cytosolic domain 44 amino acids in length, containing tyrosines at positions $Y_3$ and $Y_{15}$ which may be instrumental in signal transduction or endocytosis. MCTL is 201 amino acids long and has one potential glycoslyation site at $N_{169}$ in the extracellular carbohydrate binding domain.

The MCTL Coding Sequences

The nucleic acid and amino acid sequences of MCTL are shown in FIGS. 1A, 1B, and 1C. In accordance with the invention, any nucleic acid sequence which encodes the amino acid sequence of MCTL can be used to generate recombinant molecules which express MCTL. In a specific embodiment described herein, a partial sequence of MCTL was first isolated as Incyte Clone 515847 from a human macrophage cDNA library (MMLR1DT01).

It will be appreciated by those skilled in the art that as a result of the degeneracy of the genetic code, a multitude of MCTL-encoding nucleotide sequences, some bearing minimal homology to the nucleotide sequences of any known and naturally occurring gene may be produced. The invention has specifically contemplated each and every possible variation of nucleotide sequence that could be made by selecting combinations based on possible codon choices. These combinations are made in accordance with the standard triplet genetic code as applied to the nucleotide sequence of naturally occurring MCTL, and all such variations are to be considered as being specifically disclosed.

Although nucleotide sequences which encode MCTL and its variants are preferably capable of hybridizing to the nucleotide sequence of the naturally occurring mctl under appropriately selected conditions of stringency, it may be advantageous to produce nucleotide sequences encoding MCTL or its derivatives possessing a substantially different codon usage. Codons may be selected to increase the rate at which expression of the peptide occurs in a particular prokaryotic or eukaryotic expression host in accordance with the frequency with which particular codons are utilized by the host. Other reasons for substantially altering the nucleotide sequence encoding MCTL and its derivatives without altering the encoded amino acid sequences include the production of RNA transcripts having more desirable properties, such as a greater half-life, than transcripts produced from the naturally occurring sequence.

It is now possible to produce a DNA sequence, or portions thereof, encoding a MCTL and its derivatives entirely by synthetic chemistry, after which the synthetic gene may be inserted into any of the many available DNA vectors and cell systems using reagents that are well known in the art at the time of the filing of this application. Moreover, synthetic chemistry may be used to introduce mutations into a mctl sequence or any portion thereof.

Also included within the scope of the present invention are polynucleotide sequences that are capable of hybridizing to the nucleotide sequence of FIGS. 1A, 1B and 1C under various conditions of stringency. Hybridization conditions are based on the melting temperature (Tm) of the nucleic acid binding complex or probe, as taught in Berger and Kimmel (1987, *Guide to Molecular Cloning Techniques, Methods in Enzymology*, Vol 152, Academic Press, San Diego Calif.) incorporated herein by reference, and confer may be used at a defined "stringency" as explained below.

"Maximum stringency" typically occurs at about Tm-5° C. (5° C. below the Tm of the probe); "high stringency" at about 5° C. to 10° C. below Tm; "intermediate stringency" at about 10° C. to 20° C. below Tm; and "low stringency" at about 20° C. to 25° C. below Tm. As will be understood by those of skill in the art, a maximum stringency hybridization can be used to identify or detect identical polynucleotide sequences while an intermediate (or low) stringency hybridization can be used to identify or detect similar or related polynucleotide sequences.

The term "hybridization" as used herein shall include "any process by which a strand of nucleic acid joins with a complementary strand through base pairing" (Coombs J (1994) *Dictionary of Biotechnology*, Stockton Press, New York N.Y.). Amplification as carried out in the polymerase chain reaction technologies described in Dieffenbach CW and GS Dveksler (1995, *PCR Primer, a Laboratory Manual*, Cold Spring Harbor Press, Plainview N.Y.).

A "deletion" is defined as a change in either nucleotide or amino acid sequence in which one or more nucleotides or amino acid residues, respectively, are absent.

An "insertion" or "addition" is that change in a nucleotide or amino acid sequence which has resulted in the addition of one or more nucleotides or amino acid residues, respectively, as compared to the naturally occurring mctl or MCTL.

A "substitution" results from the replacement of one or more nucleotides or amino acids by different nucleotides or amino acids, respectively.

Altered mctl nucleic acid sequences which may be used in accordance with the invention include deletions, insertions or substitutions of different nucleotides resulting in a polynucleotide that encodes the same or a functionally equivalent MCTL. The protein may also show deletions, insertions or substitutions of amino acid residues which produce a silent change and result in a functionally equivalent MCTL. Deliberate amino acid substitutions may be made on the basis of similarity in polarity, charge, solubility, hydrophobicity, hydrophilicity, and/or the amphipathic nature of the residues as long as the biological activity of MCTL is retained. For example, negatively charged amino acids include aspartic acid and glutamic acid; positively charged amino acids include lysine and arginine; and amino acids with uncharged polar head groups having similar hydrophilicity values include leucine, isoleucine, valine; glycine, alanine; asparagine, glutamine; serine, threonine phenylalanine, and tyrosine.

Included within the scope of the present invention are alleles of mctl. As used herein, an "allele" or "allelic sequence" is an alternative form of mctl. Alleles result from a mutation, ie, a change in the nucleic acid sequence, and generally produce altered mRNAs or polypeptides whose structure or function may or may not be altered. Any given gene may have none, one or many allelic forms. Common mutational changes which give rise to alleles are generally ascribed to natural deletions, additions or substitutions of amino acids. Each of these types of changes may occur alone, or in combination with the others, one or more times in a given sequence.

Methods for DNA sequencing are well known in the art and employ such enzymes as the Klenow fragment of DNA polymerase I, SEQUENASE (US Biochemical Corp, Cleveland Ohio)), Taq polymerase (Perkin Elmer, Norwalk Conn.), thermostable T7 polymerase (Amersham, Chicago Ill.), or combinations of recombinant polymerases and proofreading exonucleases such as the ELONGASE Amplification System marketed by Gibco BRL (Gaithersburg Md.). Preferably, the process is automated with machines such as the Hamilton Micro Lab 2200 (Hamilton, Reno Nev.), Peltier Thermal Cycler (PTC200; MJ Research, Watertown Mass.) and the ABI 377 DNA sequencers (Perkin Elmer).

Extending the Polynucleotide Sequence

The polynucleotide sequence of mctl may be extended utilizing partial nucleotide sequence and various methods known in the art to detect upstream sequences such as promoters and regulatory elements. Gobinda et al (1993; PCR Methods Applic 2:318–22) disclose "restriction-site" polymerase chain reaction (PCR) as a direct method which uses universal primers to retrieve unknown sequence adjacent to a known locus. First, genomic DNA is amplified in the presence of primer to a linker sequence and a primer specific to the known region. The amplified sequences are subjected to a second round of PCR with the same linker primer and another specific primer internal to the first one. Products of each round of PCR are transcribed with an appropriate RNA polymerase and sequenced using reverse transcriptase.

Inverse PCR can be used to amplify or extend sequences using divergent primers based on a known region (Triglia T et al (1988) Nucleic Acids Res 16:8186). The primers may be designed using OLIGO® 4.06 Primer Analysis Software (1992; National Biosciences Inc, Plymouth Minn.), or another appropriate program, to be 22–30 nucleotides in length, to have a GC content of 50% or more, and to anneal to the target sequence at temperatures about 68°–72° C. The method uses several restriction enzymes to generate a suitable fragment in the known region of a gene. The fragment is then circularized by intramolecular ligation and used as a PCR template.

Capture PCR (Lagerstrom M et al (1991) PCR Methods Applic 1:111–19) is a method for PCR amplification of DNA fragments adjacent to a known sequence in human and yeast artificial chromosome DNA. Capture PCR also requires multiple restriction enzyme digestions and ligations to place an engineered double-stranded sequence into an unknown portion of the DNA molecule before PCR.

Parker JD et al (1991; Nucleic Acids Res 19:3055–60), teach walking PCR, a method for targeted gene walking which permits retrieval of unknown sequence. PROMOTERFINDER a new kit available from Clontech (Palo Alto Calif.) uses PCR, nested primers and PROMOTERFINDER libraries to walk in genomic DNA. This process avoids the need to screen libraries and is useful in finding intron/exon junctions.

Preferred libraries for screening for full length cDNAs are ones that have been size-selected to include larger cDNAs. Also, random primed libraries are preferred in that they will contain more sequences which contain the 5' and upstream regions of genes. A randomly primed library may be particularly useful if an oligo d(T) library does not yield a full-length cDNA. Genomic libraries are useful for extension into the 5'nontranslated regulatory region.

A new method for analyzing either the size or confirming the nucleotide sequence of sequencing or PCR products is capillary electrophoresis. Systems for rapid sequencing are available from Perkin Elmer, Beckman Instruments (Fullerton Calif.), and other companies. Capillary sequencing employs flowable polymers for electrophoretic separation, four different fluorescent dyes (one for each nucleotide) which are laser activated, and detection of the emitted wavelengths by a charge coupled device camera. Output/light intensity is converted to electrical signal using appropriate software (eg. GENOTYPER and SEQUENCE NAVIGATOR from Perkin Elmer) and the entire process from loading of samples to computer analysis and electronic data display is computer controlled. Capillary electrophoresis is particularly suited to the sequencing of small pieces of DNA which might be present in limited amounts in a particular sample. The reproducible sequencing of up to 350 bp of M13 phage DNA in 30 min has been reported (Ruiz-Martinez MC et al (1993) Anal Chem 65:2851–8).

Expression of the Nucleotide Sequence

In accordance with the present invention, polynucleotide sequences which encode MCTL, fragments of the polypeptide, fusion proteins or functional equivalents thereof may be used in recombinant DNA molecules that direct the expression of MCTL in appropriate host cells. Due to the inherent degeneracy of the genetic code, other DNA sequences which encode substantially the same or a functionally equivalent amino acid sequence, may be used to clone and express MCTL. As will be understood by those of skill in the art, it may be advantageous to produce MCTL-encoding nucleotide sequences possessing non-naturally occurring codons. Codons preferred by a particular prokaryotic or eukaryotic host (Murray E et al (1989) Nuc Acids Res 17:477–508) can be selected, for example, to increase the rate of MCTL expression or to produce recombinant RNA transcripts having desirable properties, such as a longer half-life, than transcripts produced from naturally occurring sequence.

The nucleotide sequences of the present invention can be engineered in order to alter a mctl coding sequence for a variety of reasons, including but not limited to, alterations which modify the cloning, processing and/or expression of the gene product. For example, mutations may be introduced using techniques which are well known in the art, eg, site-directed mutagenesis to insert new restriction sites, to alter glycosylation patterns, to change codon preference, to produce splice variants, etc.

In another embodiment of the invention, a natural, modified or recombinant mctl sequence may be ligated to a heterologous sequence to encode a fusion protein. For example, for screening of peptide libraries for inhibitors of MCTL activity, it may be useful to encode a chimeric MCTL protein that is recognized by a commercially available antibody. A fusion protein may also be engineered to contain a cleavage site located between a MCTL sequence and the heterologous protein sequence, so that the MCTL may be cleaved and substantially purified away from the heterologous moiety.

In an alternate embodiment of the invention, the coding sequence of mctl could be synthesized, whole or in part, using chemical methods well known in the art (see Caruthers MH et al (1980) Nuc Acids Res Symp Ser 215–23, Horn T et al(1980) Nuc Acids Res Symp Ser 225–32, etc). Alternatively, the protein itself could be produced using chemical methods to synthesize a MCTL amino acid sequence, whole or in part. For example, peptide synthesis can be performed using various solid-phase techniques (Roberge JY et al (1995) Science 269:202–204) and automated synthesis may be achieved, for example, using the ABI 431A Peptide Synthesizer (Perkin Elmer) in accordance with the instructions provided by the manufacturer.

The newly synthesized peptide can be substantially purified by preparative high performance liquid chromatography (eg, Creighton (1983) *Proteins, Structures and Molecular Principles,* WH Freeman and Co, New York N.Y.). The composition of the synthetic peptides may be confirmed by amino acid analysis or sequencing (eg, the Edman degradation procedure; Creighton, supra). Additionally the amino acid sequence of MCTL, or any part thereof, may be altered during direct synthesis and/or combined using chemical methods with sequences from other proteins, or any part thereof, to produce a variant polypeptide.

Expression Systems

In order to express a biologically active MCTL, the nucleotide sequence encoding MCTL or its functional equivalent, is inserted into an appropriate expression vector, ie, a vector which contains the necessary elements for the transcription and translation of the inserted coding sequence.

Methods which are well known to those skilled in the art can be used to construct expression vectors containing a MCTL coding sequence and appropriate transcriptional or translational controls. These methods include in vitro recombinant DNA techniques, synthetic techniques and in vivo recombination or genetic recombination. Such techniques are described in Sambrook et al (1989) *Molecular Cloning, A Laboratory Manual,* Cold Spring Harbor Press, Plainview N.Y. and Ausubel FM et al (1989) *Current Protocols in Molecular Biology,* John Wiley & Sons, New York N.Y.

A variety of expression vector/host systems may be utilized to contain and express a mctl coding sequence. These include but are not limited to microorganisms such as bacteria transformed with recombinant bacteriophage, plasmid or cosmid DNA expression vectors; yeast transformed with yeast expression vectors; insect cell systems infected with virus expression vectors (eg, baculovirus); plant cell systems transfected with virus expression vectors (eg, cauliflower mosaic virus, CaMV; tobacco mosaic virus, TMV) or transformed with bacterial expression vectors (eg, Ti or pBR322 plasmid); or animal cell systems.

The "control elements" or "regulatory sequences" of these systems vary in their strength and specificities and are those nontranslated regions of the vector, enhancers, promoters, and 3' untranslated regions, which interact with host cellular proteins to carry out transcription and translation. Depending on the vector system and host utilized, any number of suitable transcription and translation elements, including constitutive and inducible promoters, may be used. For example, when cloning in bacterial systems, inducible promoters such as the hybrid lacZ promoter of the BLUESCRIPT® phagemid (Stratagene, LaJolla Calif.) or PSPORT1(Gibco BRL) and ptrp-lac hybrids and the like may be used. The baculovirus polyhedrin promoter may be used in insect cells. Promoters or enhancers derived from the genomes of plant cells (eg, heat shock, RUBISCO; and storage protein genes) or from plant viruses (eg, viral promoters or leader sequences) may be cloned into the vector. In mammalian cell systems, promoters from the mammalian genes or from mammalian viruses are most appropriate. If it is necessary to generate a cell line that contains multiple copies of mctl, vectors based on SV40 or EBV may be used with an appropriate selectable marker.

In bacterial systems, a number of expression vectors may be selected depending upon the use intended for MCTL. For example, when large quantities of MCTL are needed for the induction of antibodies, vectors which direct high level expression of fusion proteins that are readily purified may be desirable. Such vectors include, but are not limited to, the multifunctional *E. coli* cloning and expression vectors such as BLUESCRIPT® (Stratagene), in which the mctl coding sequence may be ligated into the vector in frame with sequences for the amino-terminal Met and the subsequent 7 residues of β-galactosidase so that a hybrid protein is produced; pIN vectors (Van Heeke & Schuster (1989) J Biol Chem 264:5503–5509); and the like. pGEX vectors (Promega, Madison Wis.) may also be used to express foreign polypeptides as fusion proteins with glutathione S-transferase (GST). In general, such fusion proteins are soluble and can easily be purified from lysed cells by adsorption to glutathione-agarose beads followed by elution in the presence of free glutathione. Proteins made in such systems are designed to include heparin, thrombin or factor XA protease cleavage sites so that the cloned polypeptide of interest can be released from the GST moiety at will.

In the yeast, *Saccharomyces cerevisiae,* a number of vectors containing constitutive or inducible promoters such as alpha factor, alcohol oxidase and PGH may be used. For reviews, see Ausubel et al (supra) and Grant et al (1987) Methods in Enzymology 153:516–544.

In cases where plant expression vectors are used, the expression of a sequence encoding MCTL may be driven by any of a number of promoters. For example, viral promoters such as the 35S and 19S promoters of CaMV (Brisson et al (1984) Nature 310:511–514) may be used alone or in combination with the omega leader sequence from TMV (Takamatsu et al (1987) EMBO J 6:307–311). Alternatively, plant promoters such as the small subunit of RUBISCO (Coruzzi et al (1984) EMBO J 3:1671–1680; Broglie et al (1984) Science 224:838–843); or heat shock promoters (Winter J and Sinibaldi RM (1991) Results Probl Cell Differ 17:85–105) may be used. These constructs can be introduced into plant cells by direct DNA transformation or pathogen-mediated transfection. For reviews of such techniques, see Hobbs S or Murry LE in McGraw Hill *Yearbook of Science and Technology* (1992) McGraw Hill New York N.Y., pp 191–196 or Weissbach and Weissbach (1988) *Methods for Plant Molecular Biology,* Academic Press, New York N.Y., pp 421–463.

An alternative expression system which could be used to express MCTL is an insect system. In one such system,

*Autoarapha californica* nuclear polyhedrosis virus (AcNPV) is used as a vector to express foreign genes in *Spodoptera frugiperda* cells or in Trichoplusia larvae. The mctl coding sequence may be cloned into a nonessential region of the virus, such as the polyhedrin gene, and placed under control of the polyhedrin promoter. Successful insertion of mctl will render the polyhedrin gene inactive and produce recombinant virus lacking protein coat. The recombinant viruses are then used to infect *S. frugiperda* cells or Trichoplusia larvae in which MCTL is expressed (Smith et al (1983) J Virol 46:584; Engelhard EK et al (1994) Proc Nat Acad Sci 91:3224–7).

In mammalian host cells, a number of viral-based expression systems may be utilized. In cases where an adenovirus is used as an expression vector, a mctl coding sequence may be ligated into an adenovirus transcription/translation complex consisting of the late promoter and tripartite leader sequence. Insertion in a nonessential E1 or E3 region of the viral genome will result in a viable virus capable of expressing MCTL in infected host cells (Logan and Shenk (1984) Proc Natl Acad Sci 81:3655–59). In addition, transcription enhancers, such as the rous sarcoma virus (RSV) enhancer, may be used to increase expression in mammalian host cells.

Specific initiation signals may also be required for efficient translation of a mctl sequence. These signals include the ATG initiation codon and adjacent sequences. In cases where mctl, its initiation codon and upstream sequences are inserted into the appropriate expression vector, no additional translational control signals may be needed. However, in cases where only coding sequence, or a portion thereof, is inserted, exogenous transcriptional control signals including the ATG initiation codon must be provided. Furthermore, the initiation codon must be in the correct reading frame to ensure transcription of the entire insert. Exogenous transcriptional elements and initiation codons can be of various origins, both natural and synthetic. The efficiency of expression may be enhanced by the inclusion of enhancers appropriate to the cell system in use (Scharf D et al (1994) Results Probl Cell Differ 20:125–62; Bittner et al (1987) Methods in Enzymol 153:516–544).

In addition, a host cell strain may be chosen for its ability to modulate the expression of the inserted sequences or to process the expressed protein in the desired fashion. Such modifications of the polypeptide include, but are not limited to, acetylation, carboxylation, glycosylation, phosphorylation, lipidation and acylation. Post-translational processing which cleaves a "prepro" form of the protein may also be important for correct insertion, folding and/or function. Different host cells such as CHO, HeLa, MDCK, 293, WI38, etc have specific cellular machinery and characteristic mechanisms for such post-translational activities and may be chosen to ensure the correct modification and processing of the introduced, foreign protein.

For long-term, high-yield production of recombinant proteins, stable expression is preferred. For example, cell lines which stably express mctl may be transformed using expression vectors which contain viral origins of replication or endogenous expression elements and a selectable marker gene. Following the introduction of the vector, cells may be allowed to grow for 1–2 days in an enriched media before they are switched to selective media. The purpose of the selectable marker is to confer resistance to selection, and its presence allows growth and recovery of cells which successfully express the introduced sequences. Resistant clumps of stably transformed cells can be proliferated using tissue culture techniques appropriate to the cell type.

Any number of selection systems may be used to recover transformed cell lines. These include, but are not limited to, the herpes simplex virus thymidine kinase (Wigler M et al (1977) Cell 11:223–32) and adenine phosphoribosyltransferase (Lowy I et al (1980) Cell 22:817–23) genes which can be employed in tk- or aprt- cells, respectively. Also, antimetabolite, antibiotic or herbicide resistance can be used as the basis for selection; for example, dhfr which confers resistance to methotrexate (Wigler M et al (1980) Proc Natl Acad Sci 77:3567–70); npt, which confers resistance to the aminoglycosides neomycin and G-418 (Colbere-Garapin F et al (1981) J Mol Biol 150:1–14) and als or pat, which confer resistance to chlorsulfuron and phosphinotricin acetyltransferase, respectively (Murry, supra). Additional selectable genes have been described, for example, trpB, which allows cells to utilize indole in place of tryptophan, or hisD, which allows cells to utilize histinol in place of histidine (Hartman SC and RC Mulligan (1988) Proc Natl Acad Sci 85:8047–51). Recently, the use of visible markers has gained popularity with such markers as anthocyanins, β glucuronidase and its substrate, GUS, and luciferase and its substrate, luciferin, being widely used not only to identify transformants, but also to quantify the amount of transient or stable protein expression attributable to a specific vector system (Rhodes Calif. et al (1995) Methods Mol Biol 55:121–131).

Identification of Transformants Containing the Polynucleotide Sequence

Although the presence/absence of marker gene expression suggests that the gene of interest is also present, its presence and expression should be confirmed. For example, if the mctl is inserted within a marker gene sequence, recombinant cells containing mctl can be identified by the absence of marker gene function. Alternatively, a marker gene can be placed in tandem with a MCTL sequence under the control of a single promoter. Expression of the marker gene in response to induction or selection usually indicates expression of the tandem mctl as well.

Alternatively, host cells which contain the coding sequence for mctl and express MCTL may be identified by a variety of procedures known to those of skill in the art. These procedures include, but are not limited to, DNA-DNA or DNA-RNA hybridization and protein bioassay or immunoassay techniques which include membrane, solution, or chip based technologies for the detection and/or quantification of the nucleic acid or protein.

The presence of the mctl polynucleotide sequence can be detected by DNA-DNA or DNA-RNA hybridization or amplification using probes, portions or fragments of mctl. Nucleic acid amplification based assays involve the use of oligonucleotides or oligomers based on the mctl sequence to detect transformants containing mctl DNA or RNA. As used herein "oligonucleotides" or "oligomers" refer to a nucleic acid sequence of at least about 10 nucleotides and as many as about 60 nucleotides, preferably about 15 to 30 nucleotides, and more preferably about 20–25 nucleotides which can be used as a probe or amplimer.

A variety of protocols for detecting and measuring the expression of MCTL, using either polyclonal or monoclonal antibodies specific for the protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on MCTL is preferred, but a competitive binding assay may be employed. These and other assays are described, among other places, in Hampton R et al (1990, *Serological Methods, a Laboratory Manual,* APS Press, St Paul Minn.) and Maddox DE et al (1983, J Exp Med 158:1211).

A wide variety of labels and conjugation techniques are known by those skilled in the art and can be used in various nucleic acid and amino acid assays. Means for producing labeled hybridization or PCR probes for detecting sequences related to mctl include oligolabeling, nick translation, end-labeling or PCR amplification using a labeled nucleotide. Alternatively, the mctl sequence, or any portion of it, may be cloned into a vector for the production of an mRNA probe. Such vectors are known in the art, are commercially available, and may be used to synthesize RNA probes in vitro by addition of an appropriate RNA polymerase such as T7, T3 or SP6 and labeled nucleotides.

A number of companies such as Pharmacia Biotech (Piscataway N.J.), Promega (Madison Wis.), and US Biochemical Corp (Cleveland Ohio) supply commercial kits and protocols for these procedures. Suitable reporter molecules or labels include those radionuclides, enzymes, fluorescent, chemiluminescent, or chromogenic agents as well as substrates, cofactors, inhibitors, magnetic particles and the like. Patents teaching the use of such labels include U.S. Pat. Nos. 3,817,837; 3,850,752; 3,939,350; 3,996,345; 4,277,437; 4,275,149 and 4,366,241. Also, recombinant immunoglobulins may be produced as shown in U.S. Pat. No. 4,816,567 incorporated herein by reference.

Purification of MCTL

Host cells transformed with a mctl nucleotide sequence may be cultured under conditions suitable for the expression and recovery of the encoded protein from cell culture. The protein produced by a recombinant cell may be contained intracellularly or secreted depending on the sequence and/or the vector used. As will be understood by those of skill in the art, expression vectors containing mctl can be designed for efficient production and proper transmembrane insertion of MCTL into a prokaryotic or eukaryotic cell membrane. Alternatively, expression vectors containing an mctl fragment encoding primarily the soluble extracellular carbohydrate binding domain can be designed with signal sequences which direct secretion of the domain through a prokaryotic or eukaryotic cell membrane. Other recombinant constructions may join mctl or a fragment thereof to nucleotide sequence encoding a polypeptide domain which will facilitate purification of soluble proteins (Kroll DJ et al (1993) DNA Cell Biol 12:441–53; cf discussion of vectors infra containing fusion proteins).

MCTL may also be expressed as a recombinant protein with one or more additional polypeptide domains added to facilitate protein purification. Such purification facilitating domains include, but are not limited to, metal chelating peptides such as histidine-tryptophan modules that allow purification on immobilized metals, protein A domains that allow purification on immobilized immunoglobulin, and the domain utilized in the FLAGS extension/affinity purification system (Immunex Corp, Seattle Wash.). The inclusion of a cleavable linker sequences such as Factor XA or enterokinase (Invitrogen, San Diego Calif.) between the purification domain and MCTL is useful to facilitate purification. One such expression vector provides for expression of a fusion protein compromising an MCTL and contains nucleic acid encoding 6 histidine residues followed by thioredoxin and an enterokinase cleavage site. The histidine residues facilitate purification on IMIAC (immobilized metal ion affinity chromatography as described in Porath et al (1992) Protein Expression and Purification 3: 263–281) while the enterokinase cleavage site provides a means for purifying the lectin from the fusion protein.

In addition to recombinant production, fragments of MCTL may be produced by direct peptide synthesis using solid-phase techniques (cf Stewart et al (1969) *Solid-Phase Peptide Synthesis,* WH Freeman Co, San Francisco; Merrifield J (1963) J Am Chem Soc 85:2149–2154). In vitro protein synthesis may be performed using manual techniques or by automation. Automated synthesis may be achieved, for example, using Applied Biosystems 431A Peptide Synthesizer (Perkin Elmer, Foster City Calif.) in accordance with the instructions provided by the manufacturer. Various fragments of MCTL may be chemically synthesized separately and combined using chemical methods to produce the full length molecule.

Uses of MCTL

The rationale for the use of polynucleotide and polypeptide sequences disclosed herein is based in part on the structural homology among the novel MCTL and human macrophage C-type lectin, a human lymphocyte activation antigen, and the human asialoglycoprotein receptor, in particular in the extracellular carbohydrate binding domains.

In some instances it may be advantageous to supress MCTL expression or to inhibit the interaction of MCTL with a target cell. For instance, suppression of an MCTL nucleic acid sequence may alleviate damage associated with over-reaction of the immune system in the chronic rejection of transplanted tissues and organs. MCTL expression could be supressed by administration of mctl antisense oligonucleotides. Alternatively, specific antibodies against MCTL, or inhibitors of the MCTL-graft cell interaction, may be introduced to suppress the infiltration of macrophages into allograft tissue.

Another application for an inhibitor of MCTL would be in the prevention of macrophage colonization by pathogenic bacteria. For instance, pathogenic Mycobacteria, including *M. tuberculosis,* colonize in activated macrophages. The attachment of such pathogens to macrophages, via lectin molecules expressed on the macrophages, is the preliminary step in pathogenesis. Preventing this interaction may provide an important approach for blocking the colonization of host macrophages by pathogenic bacteria or parasites. Specific inhibitors or antibodies may be developed against MCTL, or MCTL expression in macrophages may be turned off by using antisense technologies.

In a preferred embodiment, a soluble fragment of MCTL consisting primarily of the extracellular carbohydrate binding domain may be used as an inhibitor of MCTL. The structural integrity of the isolated carbohydrate domain would be maintained by the 3 intrachain disulfides. When administered, the soluble binding domain may block MCTL-target cell interactions by “out-competing” MCTL for ligands on the surface of the target cell.

MCTL may be exploited for the purposes of targeted drug delivery. Anti-pathogen and anti-parasite therapies are hampered by the sequestering of the pathogenic bacteria or parasites within macrophages, restricting the bioavailability of potentially useful drugs. A drug may be targeted to the infected macrophages by means of a sugar molecule covalently attached to the drug, which would bind to MCTL expressed on the surface of the macrophage. The MCTL-bound drug-sugar conjugate would subsequently be internalized into the infected macrophage, enhancing the bioavailability and efficacy of the drug.

Macrophages or other immune cells expressing MCTL could alternatively serve as conduits for the directed delivery of therapeutic agents to diseased cells. The therapeutic agent, or the gene encoding the therapeutic agent, may be introduced into macrophages, or macrophage-precursor stem cells, expressing MCTL. The macrophages would interact specifically with diseased cells displaying surface molecules recognized by MCTL, delivering the drug when endocytosis of the diseased target cell occurred. MCTL may also be incorporated into lipid vesicles containing a therapeutic agent. The vesicles would interact with diseased cells displaying surface molecules recognized by MCTL, delivering the drug to the desired target.

Tumor cells may be treated with agents to alter the structures of target cell-surface carbohydrates to enhance the specificity of target cell/macrophage recognition via MCTL. This is particularly advantageous if MCTL recognizes "unusual" sugars which are not normally present in the host, but can be produced in tumor cells by the administration of drugs that alter the synthesis of surface carbohydrates in the rapidly-growing tumor cells.

MCTL Antibodies

MCTL-specific antibodies are useful for the diagnosis of conditions and diseases associated with expression of MCTL. MCTL for antibody induction does not require biological activity; however, the protein fragment, or oligopeptide must be antigenic. Peptides used to induce specific antibodies may have an amino acid sequence consisting of at least five amino acids, preferably at least 10 amino acids. They should mimic a portion of the amino acid sequence of the natural protein and may contain the entire amino acid sequence of a small, naturally occurring molecule. Short stretches of MCTL amino acids may be fused with those of another protein such as keyhole limpet hemocyanin and antibody produced against the chimeric molecule. Procedures well known in the art can be used for the production of antibodies to MCTL. Such antibodies include, but are not limited to, polyclonal, monoclonal, chimeric, single chain, Fab fragments and fragments produced by a Fab expression library. Neutralizing antibodies, ie, those which inhibit dimer formation, are especially preferred for diagnostics and therapeutics.

For the production of antibodies, various hosts including goats, rabbits, rats, mice, etc may be immunized by injection with MCTL or any portion, fragment or oligopeptide which retains immunogenic properties. Depending on the host species, various adjuvants may be used to increase immunological response. Such adjuvants include but are not limited to Freund's, mineral gels such as aluminum hydroxide, and surface active substances such as lysolecithin, pluronic polyols, polyanions, peptides, oil emulsions, keyhole limpet hemocyanin, and dinitrophenol. BCG (bacilli Calmette-Guerin) and *Corynebacterium parvum* are potentially useful human adjuvants.

Monoclonal antibodies to MCTL may be prepared using any technique which provides for the production of antibody molecules by continuous cell lines in culture. These include but are not limited to the hybridoma technique originally described by Koehler and Milstein (1975 Nature 256:495–497), the human B-cell hybridoma technique (Kosbor et al (1983) Immunol Today 4:72; Cote et al (1983) Proc Natl Acad Sci 80:2026–2030) and the EBV-hybridoma technique (Cole et al (1985) *Monoclonal Antibodies and Cancer Therapy,* Alan R Liss Inc, New York N.Y., pp 77–96).

In addition, techniques developed for the production of "chimeric antibodies", the splicing of mouse antibody genes to human antibody genes to obtain a molecule with appropriate antigen specificity and biological activity can be used (Morrison et al (1984) Proc Natl Acad Sci 81:6851–6855; Neuberger et al (1984) Nature 312:604–608; Takeda et al (1985) Nature 314:452–454). Alternatively, techniques described for the production of single chain antibodies (U.S. Pat. No. 4,946,778) can be adapted to produce MCTL-specific single chain antibodies Antibodies may also be produced by inducing in vivo production in the lymphocyte-population or by screening recombinant immunoglobulin libraries or panels of highly specific binding reagents as disclosed in Orlandi et al (1989, Proc Natl Acad Sci 86: 3833–3837), and Winter G and Milstein C (1991; Nature 349:293–299).

Antibody fragments which contain specific binding sites for MCTL may also be generated. For example, such fragments include, but are not limited to, the F(ab')2 fragments which can be produced by pepsin digestion of the antibody molecule and the Fab fragments which can be generated by reducing the disulfide bridges of the F(ab')2 fragments. Alternatively, Fab expression libraries may be constructed to allow rapid and easy identification of monoclonal Fab fragments with the desired specificity (Huse WD et al (1989) Science 256:1275–1281).

A variety of protocols for competitive binding or immunoradiometric assays using either polyclonal or monoclonal antibodies with established specificities are well known in the art. Such immunoassays typically involve the formation of complexes between MCTL and its specific antibody and the measurement of complex formation. A two-site, monoclonal-based immunoassay utilizing monoclonal antibodies reactive to two noninterfering epitopes on a specific MCTL protein is preferred, but a competitive binding assay may also be employed. These assays are described in Maddox DE et al (1983, J Exp Med 158:1211).

Diagnostic Assays Using MCTL Specific Antibodies

Particular MCTL antibodies are useful for the diagnosis of conditions or diseases characterized by expression of MCTL or in assays to monitor patients being treated with MCTL, agonists or inhibitors. Diagnostic assays for MCTL include methods utilizing the antibody and a label to detect MCTL in human body fluids or extracts of cells or tissues. The polypeptides and antibodies of the present invention may be used with or without modification. Frequently, the polypeptides and antibodies will be labeled by joining them, either covalently or noncovalently, with a reporter molecule. A wide variety of reporter molecules are known, several of which were described above.

A variety of protocols for measuring MCTL, using either polyclonal or monoclonal antibodies specific for the respective protein are known in the art. Examples include enzyme-linked immunosorbent assay (ELISA), radioimmunoassay (RIA) and fluorescent activated cell sorting (FACS). A two-site, monoclonal-based immunoassay utilizing monoclonal antibodies reactive to two non-interfering epitopes on MCTL is preferred, but a competitive binding assay may be employed. These assays are described, among other places, in Maddox, DE et al (1983, J Exp Med 158:1211).

In order to provide a basis for diagnosis, normal or standard values for MCTL expression must be established. This is accomplished by combining body fluids or cell extracts taken from normal subjects, either animal or human, with antibody to MCTL under conditions suitable for complex formation which are well known in the art. The amount of standard complex formation may be quantified by comparing various artificial membranes containing known quantities of MCTL with both control and disease samples from biopsied tissues. Then, standard values obtained from normal samples may be compared with values obtained from samples from subjects potentially affected by disease. Deviation between standard and subject values establishes the presence of disease state.

Drug Screening

MCTL, its catalytic or immunogenic fragments or oligopeptides thereof, can be used for screening therapeutic compounds in any of a variety of drug screening techniques. The fragment employed in such a test may be free in solution, affixed to a solid support, borne on a cell surface, or located intracellularly. The formation of binding complexes, between MCTL and the agent being tested, may be measured.

Another technique for drug screening which provides for high throughput screening of compounds having suitable binding affinity to the MCTL is described in detail in "Determination of Amino Acid Sequence Antigenicity" by Geysen HN, WO Application 84/03564, published on Sep. 13, 1984, and incorporated herein by reference. In summary, large numbers of different small peptide test compounds are synthesized on a solid substrate, such as plastic pins or some other surface. The peptide test compounds are reacted with fragments of MCTL and washed. Bound MCTL is then detected by methods well known in the art. Substantially purified MCTL can also be coated directly onto plates for use in the aforementioned drug screening techniques. Alternatively, non-neutralizing antibodies can be used to capture the peptide and immobilize it on a solid support.

This invention also contemplates the use of competitive drug screening assays in which neutralizing antibodies capable of binding MCTL specifically compete with a test compound for binding MCTL. In this manner, the antibodies can be used to detect the presence of any peptide which shares one or more antigenic determinants with MCTL.

Uses of the Polynucleotide Encoding MCTL

A polynucleotide, MCTL, or any part thereof, may be used for diagnostic and/or therapeutic purposes. For diagnostic purposes, the MCTL of this invention may be used to detect and quantitate gene expression in biopsied tissues in which expression of MCTL may be implicated. The diagnostic assay is useful to distinguish between absence, presence, and excess expression of MCTL and to monitor regulation of MCTL levels during therapeutic intervention. Included in the scope of the invention are oligonucleotide sequences, antisense RNA and DNA molecules, and PNAs.

Another aspect of the subject invention is to provide for hybridization or PCR probes which are capable of detecting polynucleotide sequences, including genomic sequences, encoding MCTL or closely related molecules. The specificity of the probe, whether it is made from a highly specific region, eg, 10 unique nucleotides in the 5' regulatory region, or a less specific region, eg, especially in the 3' region, and the stringency of the hybridization or amplification (maximal, high, intermediate or low) will determine whether the probe identifies only naturally occurring MCTL, alleles or related sequences.

Probes may also be used for the detection of related sequences and should preferably contain at least 50% of the nucleotides from any of these MCTL encoding sequences. The hybridization probes of the subject invention may be derived from the nucleotide sequence of SEQ ID NO:2 or from genomic sequence including promoter, enhancer elements and introns of the naturally occurring MCTL. Hybridization probes may be labeled by a variety of reporter groups, including radionuclides such as 32P or 35S, or enzymatic labels such as alkaline phosphatase coupled to the probe via avidin/biotin coupling systems, and the like.

Other means for producing specific hybridization probes for MCTL DNAs include the cloning of nucleic acid sequences encoding MCTL or MCTL derivatives into vectors for the production of mRNA probes. Such vectors are known in the art and are commercially available and may be used to synthesize RNA probes in vitro by means of the addition of the appropriate RNA polymerase as T7 or SP6 RNA polymerase and the appropriate radioactively labeled nucleotides.

Diagnostics

Polynucleotide sequences encoding MCTL may be used for the diagnosis of conditions or diseases with which the expression of MCTL is associated. For example, polynucleotide sequences encoding MCTL may be used in hybridization or PCR assays of fluids or tissues from biopsies to detect MCTL expression. The form of such qualitative or quantitative methods may include Southern or northern analysis, dot blot or other membrane-based technologies; PCR technologies; dip stick, pin, chip and ELISA technologies. All of these techniques are well known in the art and are the basis of many commercially available diagnostic kits.

The MCTL nucleotide sequences disclosed herein provide the basis for assays that detect activation or induction associated with inflammation or disease. The MCTL nucleotide sequence may be labeled by methods known in the art and added to a fluid or tissue sample from a patient under conditions suitable for the formation of hybridization complexes. After an incubation period, the sample is washed with a compatible fluid which optionally contains a dye (or other label requiring a developer) if the nucleotide has been labeled with an enzyme. After the compatible fluid is rinsed off, the dye is quantitated and compared with a standard. If the amount of dye in the biopsied or extracted sample is significantly elevated over that of a comparable control sample, the nucleotide sequence has hybridized with nucleotide sequences in the sample, and the presence of elevated levels of MCTL nucleotide sequences in the sample indicates the presence of the associated inflammation and/or disease.

Such assays may also be used to evaluate the efficacy of a particular therapeutic treatment regime in animal studies, in clinical trials, or in monitoring the treatment of an individual patient. In order to provide a basis for the diagnosis of disease, a normal or standard profile for MCTL expression must be established. This is accomplished by combining body fluids or cell extracts taken from normal subjects, either animal or human, with MCTL, or a portion thereof, under conditions suitable for hybridization or amplification. Standard hybridization may be quantified by comparing the values obtained for normal subjects with a dilution series of MCTL run in the same experiment where a known amount of substantially purified MCTL is used. Standard values obtained from normal samples may be compared with values obtained from samples from patients affected by MCTL-associated diseases. Deviation between standard and subject values establishes the presence of disease.

Once disease is established, a therapeutic agent is administered and a treatment profile is generated. Such assays may be repeated on a regular basis to evaluate whether the values in the profile progress toward or return to the normal or standard pattern. Successive treatment profiles may be used to show the efficacy of treatment over a period of several days or several months.

PCR as described in U.S. Pat. Nos. 4,683,195 and 4,965,188 provides additional uses for oligonucleotides based upon the MCTL sequence. Such oligomers are generally chemically synthesized, but they may be generated enzymatically or produced from a recombinant source. Oligomers generally comprise two nucleotide sequences, one with sense orientation (5'->3') and one with antisense (3'<-5'), employed under optimized conditions for identification of a specific gene or condition. The same two oligomers, nested sets of oligomers, or even a degenerate pool of oligomers may be employed under less stringent conditions for detection and/or quantitation of closely related DNA or RNA sequences.

Additionally, methods to quantitate the expression of a particular molecule include radiolabeling (Melby PC et al 1993 J Immunol Methods 159:235–44) or biotinylating (Duplaa C et al 1993 Anal Biochem 229–36) nucleotides, coamplification of a control nucleic acid, and standard curves onto which the experimental results are interpolated. Quantitation of multiple samples may be speeded up by running the assay in an ELISA format where the oligomer of interest is presented in various dilutions and a spectrophotometric or colorimetric response gives rapid quantitation. A definitive diagnosis of this type may allow health professionals to begin aggressive treatment and prevent further worsening of the condition. Similarly, further assays can be used to monitor the progress of a patient during treatment. Furthermore, the nucleotide sequences disclosed herein may be used in molecular biology techniques that have not yet been developed, provided the new techniques rely on properties of nucleotide sequences that are currently known such as the triplet genetic code, specific base pair interactions, and the like.

Therapeutics

Based upon its homology to the gene encoding human macrophage lectin 2 and its expression profile, the MCTL polynucleotide disclosed herein may be useful in the treatment of disorders such as graft rejection, autoimmune disease, bacterial and parasitic infections, and cancer.

Expression vectors derived from retroviruses, adenovirus, herpes or vaccinia viruses, or from various bacterial plasmids, may be used for delivery of nucleotide sequences to the targeted organ, tissue or cell population. Methods which are well known to those skilled in the art can be used to construct recombinant vectors which will express antisense MCTL. See, for example, the techniques described in Sambrook et al (supra) and Ausubel et al (supra).

The polynucleotides comprising full length cDNA sequence and/or its regulatory elements enable researchers to use MCTL as an investigative tool in sense (Youssoufian H and HF Lodish 1993 Mol Cell Biol 13:98–104) or antisense (Eguchi et al (1991) Annu Rev Biochem 60:631–652) regulation of gene function. Such technology is now well known in the art, and sense or antisense oligomers, or larger fragments, can be designed from various locations along the coding or control regions.

Genes encoding MCTL can be turned off by transfecting a cell or tissue with expression vectors which express high levels of a desired MCTL fragment. Such constructs can flood cells with untranslatable sense or antisense sequences. Even in the absence of integration into the DNA, such vectors may continue to transcribe RNA molecules until all copies are disabled by endogenous nucleases. Transient expression may last for a month or more with a non-replicating vector (Mettler I, personal communication) and even longer if appropriate replication elements are part of the vector system.

As mentioned above, modifications of gene expression can be obtained by designing antisense molecules, DNA, RNA or PNA, to the control regions of MCTL, ie, the promoters, enhancers, and introns. Oligonucleotides derived from the transcription initiation site, eg, between –10 and +10 regions of the leader sequence, are preferred. The antisense molecules may also be designed to block translation of mRNA by preventing the transcript from binding to ribosomes. Similarly, inhibition can be achieved using "triple helix" base-pairing methodology. Triple helix pairing compromises the ability of the double helix to open sufficiently for the binding of polymerases, transcription factors, or regulatory molecules. Recent therapeutic advances using triplex DNA were reviewed by Gee JE et al (In: Huber BE and BI Carr (1994) *Molecular and Immunologic Approaches,* Futura Publishing Co, Mt Kisco N.Y.).

Ribozymes are enzymatic RNA molecules capable of catalyzing the specific cleavage of RNA. The mechanism of ribozyme action involves sequence-specific hybridization of the ribozyme molecule to complementary target RNA, followed by endonucleolytic cleavage. Within the scope of the invention are engineered hammerhead motif ribozyme molecules that can specifically and efficiently catalyze endonucleolytic cleavage of MCTL.

Specific ribozyme cleavage sites within any potential RNA target are initially identified by scanning the target molecule for ribozyme cleavage sites which include the following sequences, GUA, GUU and GUC. Once identified, short RNA sequences of between 15 and 20 ribonucleotides corresponding to the region of the target gene containing the cleavage site may be evaluated for secondary structural features which may render the oligonucleotide inoperable. The suitability of candidate targets may also be evaluated by testing accessibility to hybridization with complementary oligonucleotides using ribonuclease protection assays.

Antisense molecules and ribozymes of the invention may be prepared by any method known in the art for the synthesis of RNA molecules. These include techniques for chemically synthesizing oligonucleotides such as solid phase phosphoramidite chemical synthesis. Alternatively, RNA molecules may be generated by in vitro and in vivo transcription of DNA sequences encoding MCTL. Such DNA sequences may be incorporated into a wide variety of vectors with suitable RNA polymerase promoters such as T7 or SP6. Alternatively, antisense cDNA constructs that synthesize antisense RNA constitutively or inducibly can be introduced into cell lines, cells or tissues.

RNA molecules may be modified to increase intracellular stability and half-life. Possible modifications include, but are not limited to, the addition of flanking sequences at the 5' and/or 3' ends of the molecule or the use of phosphorothioate or 2' O-methyl rather than phosphodiesterase linkages within the backbone of the molecule. This concept is inherent in the production of PNAs and can be extended in all of these molecules by the inclusion of nontraditional bases such as inosine, queosine and wybutosine as well as acetyl-, methyl-, thio- and similarly modified forms of adenine, cytidine, guanine, thymine, and uridine which are not as easily recognized by endogenous endonucleases.

Methods for introducing vectors into cells or tissues include those methods discussed infra and which are equally suitable for in vivo, in vitro and ex vivo therapy. For ex vivo therapy, vectors are introduced into stem cells taken from the patient and clonally propagated for autologous transplant back into that same patient is presented in U.S. Pat. Nos. 5,399,493 and 5,437,994, disclosed herein by reference. Delivery by transfection and by liposome are quite well known in the art.

Furthermore, the nucleotide sequences for MCTL disclosed herein may be used in molecular biology techniques that have not yet been developed, provided the new techniques rely on properties of nucleotide sequences that are currently known, including but not limited to such properties as the triplet genetic code and specific base pair interactions.

Detection and Mapping of Related Polynucleotide Sequences

The nucleic acid sequence for MCTL can also be used to generate hybridization probes for mapping the naturally occurring genomic sequence. The sequence may be mapped to a particular chromosome or to a specific region of the chromosome using well known techniques. These include in situ hybridization to chromosomal spreads, flow-sorted chromosomal preparations, or artificial chromosome constructions such as yeast artificial chromosomes, bacterial artificial chromosomes, bacterial P1 constructions or single chromosome cDNA libraries as reviewed in Price CM (1993; Blood Rev 7:127–34) and Trask BJ (1991; Trends Genet 7:149–54).

The technique of fluorescent in situ hybridization of chromosome spreads has been described, among other places, in Verma et al (1988) *Human Chromosomes: a Manual of Basic Techniques,* Pergamon Press, New York N.Y. Fluorescent in situ hybridization of chromosomal preparations and other physical chromosome mapping techniques may be correlated with additional genetic map data. Examples of genetic map data can be found in the 1994 Genome Issue of Science (265:1981f). Correlation between the location of a MCTL on a physical chromosomal map and a specific disease (or predisposition to a specific disease) may help delimit the region of DNA associated with that genetic disease. The nucleotide sequences of the subject invention may be used to detect differences in gene sequences between normal, carrier or affected individuals.

In situ hybridization of chromosomal preparations and physical mapping techniques such as linkage analysis using established chromosomal markers are invaluable in extending genetic maps. A recent example of an STS based map of the human genome was recently published by the Whitehead-MIT Center for Genomic Research (Hudson TJ et al (1995) Science 270:1945–1954). Often the placement of a gene on the chromosome of another mammalian species such as mouse (Whitehead Institute/MIT Center for Genome Research, Genetic Map of the Mouse, Database Release 10, Apr. 28, 1995) may reveal associated markers even if the number or arm of a particular human chromosome is not known. New sequences can be assigned to chromosomal arms, or parts thereof, by physical mapping. This provides valuable information to investigators searching for disease genes using positional cloning or other gene discovery techniques. Once a disease or syndrome, such as ataxia telangiectasia (AT), has been crudely localized by genetic linkage to a particular genomic region, for example, AT to 11q22–23 (Gatti et al (1988) Nature 336:577–580), any sequences mapping to that area may represent associated or regulatory genes for further investigation. The nucleotide sequence of the subject invention may also be used to detect differences in the chromosomal location due to translocation, inversion, etc. among normal, carrier or affected individuals.

Pharmaceutical Compositions

The present invention relates to pharmaceutical compositions which may comprise nucleotides, proteins, antibodies, agonists, antagonists, or inhibitors, alone or in combination with at least one other agent, such as stabilizing compound, which may be administered in any sterile, biocompatible pharmaceutical carrier, including, but not limited to, saline, buffered saline, dextrose, and water. Any of these molecules can be administered to a patient alone, or in combination with other agents, drugs or hormones, in pharmaceutical compositions where it is mixed with excipient(s) or pharmaceutically acceptable carriers. In one embodiment of the present invention, the pharmaceutically acceptable carrier is pharmaceutically inert.

Administration of Pharmaceutical Compositions

Administration of pharmaceutical compositions is accomplished orally or parenterally. Methods of parenteral delivery include topical, intra-arterial (directly to the tumor), intramuscular, subcutaneous, intramedullary, intrathecal, intraventricular, intravenous, intraperitoneal, or intranasal administration. In addition to the active ingredients, these pharmaceutical compositions may contain suitable pharmaceutically acceptable carriers comprising excipients and auxiliaries which facilitate processing of the active compounds into preparations which can be used pharmaceutically. Further details on techniques for formulation and administration may be found in the latest edition of "Remington's Pharmaceutical Sciences" (Maack Publishing Co, Easton Pa.).

Pharmaceutical compositions for oral administration can be formulated using pharmaceutically acceptable carriers well known in the art in dosages suitable for oral administration. Such carriers enable the pharmaceutical compositions to be formulated as tablets, pills, dragees, capsules, liquids, gels, syrups, slurries, suspensions and the like, for ingestion by the patient.

Pharmaceutical preparations for oral use can be obtained through combination of active compounds with solid excipient, optionally grinding a resulting mixture, and processing the mixture of granules, after adding suitable auxiliaries, if desired, to obtain tablets or dragee cores. Suitable excipients are carbohydrate or protein fillers such as sugars, including lactose, sucrose, mannitol, or sorbitol; starch from corn, wheat, rice, potato, or other plants; cellulose such as methyl cellulose, hydroxypropylmethylcellulose, or sodium carboxymethylcellulose; and gums including arabic and tragacanth; and proteins such as gelatin and collagen. If desired, disintegrating or solubilizing agents may be added, such as the cross-linked polyvinyl pyrrolidone, agar, alginic acid, or a salt thereof, such as sodium alginate.

Dragee cores are provided with suitable coatings such as concentrated sugar solutions, which may also contain gum arabic, talc, polyvinylpyrrolidone, carbopol gel, polyethylene glycol, and/or titanium dioxide, lacquer solutions, and suitable organic solvents or solvent mixtures. Dyestuffs or pigments may be added to the tablets or dragee coatings for product identification or to characterize the quantity of active compound, ie, dosage.

Pharmaceutical preparations which can be used orally include push-fit capsules made of gelatin, as well as soft, sealed capsules made of gelatin and a coating such as glycerol or sorbitol. Push-fit capsules can contain active ingredients mixed with a filler or binders such as lactose or starches, lubricants such as talc or magnesium stearate, and, optionally, stabilizers. In soft capsules, the active compounds may be dissolved or suspended in suitable liquids, such as fatty oils, liquid paraffin, or liquid polyethylene glycol with or without stabilizers.

Pharmaceutical formulations for parenteral administration include aqueous solutions of active compounds. For injection, the pharmaceutical compositions of the invention may be formulated in aqueous solutions, preferably in physiologically compatible buffers such as Hanks's solution, Ringer's solution, or physiologically buffered saline. Aqueous injection suspensions may contain substances which increase the viscosity of the suspension, such as sodium carboxymethyl cellulose, sorbitol, or dextran. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Optionally, the suspension may also contain suitable stabilizers or agents which increase the solubility of the compounds to allow for the preparation of highly concentrated solutions.

For topical or nasal administration, penetrants appropriate to the particular barrier to be permeated are used in the formulation. Such penetrants are generally known in the art.

Manufacture ad Storage

The pharmaceutical compositions of the present invention may be manufactured in a manner that known in the art, eg, by means of conventional mixing, dissolving, granulating, dragee-making, levigating, emulsifying, encapsulating, entrapping or lyophilizing processes.

The pharmaceutical composition may be provided as a salt and can be formed with many acids, including but not limited to hydrochloric, sulfuric, acetic, lactic, tartaric, malic, succinic, etc. Salts tend to be more soluble in aqueous or other protonic solvents that are the corresponding free base forms. In other cases, the preferred preparation may be a lyophilized powder in 1 mM–50 mM histidine, 0.1%–2% sucrose, 2%–7% mannitol at a pH range of 4.5 to 5.5 that is combined with buffer prior to use.

After pharmaceutical compositions comprising a compound of the invention formulated in a acceptable carrier have been prepared, they can be placed in an appropriate container and labeled for treatment of an indicated condition. For administration of MCTL, such labeling would include amount, frequency and method of administration.

Therapeutically Effective Dose

Pharmaceutical compositions suitable for use in the present invention include compositions wherein the active ingredients are contained in an effective amount to achieve the intended purpose. The determination of an effective dose is well within the capability of those skilled in the art.

For any compound, the therapeutically effective dose can be estimated initially either in cell culture assays, eg, of neoplastic cells, or in animal models, usually mice, rabbits, dogs, or pigs. The animal model is also used to achieve a desirable concentration range and route of administration. Such information can then be used to determine useful doses and routes for administration in humans.

A therapeutically effective dose refers to that amount of protein or its antibodies, antagonists, or inhibitors which ameliorate the symptoms or condition. Therapeutic efficacy and toxicity of such compounds can be determined by standard pharmaceutical procedures in cell cultures or experimental animals, eg, ED50 (the dose therapeutically effective in 50% of the population) and LD50 (the dose lethal to 50% of the population). The dose ratio between therapeutic and toxic effects is the therapeutic index, and it can be expressed as the ratio, LD50/ED50. Pharmaceutical compositions which exhibit large therapeutic indices are preferred. The data obtained from cell culture assays and animal studies is used in formulating a range of dosage for human use. The dosage of such compounds lies preferably within a range of circulating concentrations that include the ED50 with little or no toxicity. The dosage varies within this range depending upon the dosage form employed, sensitivity of the patient, and the route of administration.

The exact dosage is chosen by the individual physician in view of the patient to be treated. Dosage and administration are adjusted to provide sufficient levels of the active moiety or to maintain the desired effect. Additional factors which may be taken into account include the severity of the disease state, eg, tumor size and location; age, weight and gender of the patient; diet, time and frequency of administration, drug combination(s), reaction sensitivities, and tolerance/response to therapy. Long acting pharmaceutical compositions might be administered every 3 to 4 days, every week, or once every two weeks depending on half-life and clearance rate of the particular formulation.

Normal dosage amounts may vary from 0.1 to 100,000 micrograms, up to a total dose of about 1 g, depending upon the route of administration. Guidance as to particular dosages and methods of delivery is provided in the literature. See U.S. Pat. Nos. 4,657,760; 5,206,344; or 5,225,212. Those skilled in the art will employ different formulations for nucleotides than for proteins or their inhibitors. Similarly, delivery of polynucleotides or polypeptides will be specific to particular cells, conditions, locations, etc.

It is contemplated, for example, that MCTL, or an MCTL fragment or derivative, can be delivered in a suitable formulation as a therapeutic agent. Similarly, administration of agonists should also improve the activity or lifespan of this protein and promote the recognition and destruction of diseased cells and pathogens. Alternatively, administration of inhibitors should alleviate tissue destruction in graft rejection and autoimmune disease.

The examples below are provided to illustrate the subject invention and are not included for the purpose of limiting the invention.

EXAMPLES

I DNA Library Construction

The normal peripheral blood macrophages used for this library were obtained from two 24 year old, Caucasian males. This library (MMLR1DT01) represents a mixture of allogeneically stimulated human macrophage populations obtained from Ficoll/Hypaque purified buffy coats. The cells from the two different donors (not typed for HLA alleles) were incubated at a density of $1 \times 10^6$/ml, cultured for 48 hours in DME containing 10% human serum.

After incubation, macrophages mostly adhered to the plastic surface of the petri dish, whereas most other cell types, B and T lymphocytes, remained in solution. The DME was decanted from the wells and the wells were washed with phosphate buffered saline (PBS). Macrophages were released from the plastic surface by gently scraping the petri dishes in PBS/1 mM EDTA. Macrophages were lysed immediately in buffer containing guanidinium isothiocyanate.

The lysate was extracted twice with a mixture of acid phenol pH 4.0 and centrifuged over a CsCl cushion using an Beckman SW28 rotor in a L8-70M Ultracentrifuge (Beckman Instruments). The RNA was precipitated using 0.3 M sodium acetate and 2.5 volumes of ethanol, resuspended in water and DNase treated for 15 min at 37° C. It must be noted that some contaminating T and B lymphocytes may also have been present.

The RNA was used in the SuperScript Plasmid System for cDNA Synthesis and Plasmid Cloning (catalogue #18248–013; Gibco BRL, Gaithersburg MD) with the recommended protocol. cDNAs were fractionated on a Sepharose CL4B column (catalog #275105, Pharmacia, and those cDNAs exceeding 400 bp were ligated into PSPORT1. The plasmid was transformed into chemically competent DH5α host cells (Gibco BRL).

II Isolation and Sequencing of cDNA Clones

Plasmid DNA was released from the cells and purified using the Miniprep Kit (Catalogue # 77468; Advanced Genetic Technologies Corporation, Gaithersburg Md.). This kit consists of a 96 well block with reagents for 960 purifications. The recommended protocol was employed except for the following changes: 1) the 96 wells were each filled with only 1 ml of sterile Terrific Broth (Catalog # 22711, LIFE TECHNOLOGIES™, Gaithersburg MD) with carbenicillin at 25 mg/L and glycerol at 0.4%; 2) the bacteria were cultured for 24 hours after the wells were inoculated and then lysed with 60 μl of lysis buffer; 3) a centrifugation step employing the Beckman GS-6R @2900 rpm for 5 min was performed before the contents of the block were added to the primary filter plate; and 4) the optional step of adding isopropanol to TRIS buffer was not routinely performed. After the last step in the protocol, samples were transferred to a Beckman 96-well block for storage.

The cDNAs were sequenced by the method of Sanger F and AR Coulson (1975; J Mol Biol 94:441f), using a Hamilton Micro Lab 2200 (Hamilton, Reno Nev.) in combination with four Peltier Thermal Cyclers (PTC200 from MJ Research, Watertown Mass.) and Applied Biosystems 377 or 373 DNA Sequencing Systems (Perkin Elmer) and reading frame was determined.

III Homology Searching of cDNA Clones and Their Deduced Proteins

Each cDNA was compared to sequences in GenBank using a search algorithm developed by Applied Biosystems and incorporated into the INHERIT- 670 Sequence Analysis System. In this algorithm, Pattern Specification Language (TRW Inc, Los Angeles Calif.) was used to determine regions of homology. The three parameters that determine how the sequence comparisons run were window size, window offset, and error tolerance. Using a combination of these three parameters, the DNA database was searched for sequences containing regions of homology to the query sequence, and the appropriate sequences were scored with an initial value. Subsequently, these homologous regions were examined using dot matrix homology plots to distinguish regions of homology from chance matches. Smith-Waterman alignments were used to display the results of the homology search.

Peptide and protein sequence homologies were ascertained using the INHERIT™ 670 Sequence Analysis System in a way similar to that used in DNA sequence homologies. Pattern Specification Language and parameter windows were used to search protein databases for sequences containing regions of homology which were scored with an initial value. Dot-matrix homology plots were examined to distinguish regions of significant homology from chance matches.

BLAST, which stands for Basic Local Alignment Search Tool (Altschul SF (1993) J Mol Evol 36:290–300; Altschul, SF et al (1990) J Mol Biol 215:403–10), was used to search for local sequence alignments. BLAST produces alignments of both nucleotide and amino acid sequences to determine sequence similarity. Because of the local nature of the alignments, BLAST is especially useful in determining exact matches or in identifying homologs. BLAST is useful for matches which do not contain gaps. The fundamental unit of BLAST algorithm output is the High-scoring Segment Pair (HSP).

An HSP consists of two sequence fragments of arbitrary but equal lengths whose alignment is locally maximal and for which the alignment score meets or exceeds a threshold or cutoff score set by the user. The BLAST approach is to look for HSPs between a query sequence and a database sequence, to evaluate the statistical significance of any matches found, and to report only those matches which satisfy the user-selected threshold of significance. The parameter E establishes the statistically significant threshold for reporting database sequence matches. E is interpreted as the upper bound of the expected frequency of chance occurrence of an HSP (or set of HSPs) within the context of the entire database search. Any database sequence whose match satisfies E is reported in the program output.

IV Northern Analysis

Northern analysis is a laboratory technique used to detect the presence of a transcript of a gene and involves the hybridization of a labelled nucleotide sequence to a membrane on which RNAs from a particular cell type or tissue have been bound (Sambrook et al. supra).

Analogous computer techniques using BLAST (Altschul SF 1993 and 1990, supra) are used to search for identical or related molecules in nucleotide databases such as GenBank or the LIFESEQ® database (Incyte, Palo Alto Calif.). This analysis is much faster than multiple, membrane-based hybridizations. In addition, the sensitivity of the computer search can be modified to determine whether any particular match is categorized as exact or homologous.

The basis of the search is the product score which is defined as:

$$\frac{\% \text{ sequence identity} \times \% \text{ maximum BLAST score}}{100}$$

and it takes into acccount both the degree of similarity between two sequences and the length of the sequence match. For example, with a product score of 40, the match will be exact within a 1–2% error; and at 70, the match will be exact. Homologous molecules are usually identified by selecting those which show product scores between 15 and 40, although lower scores may identify related molecules.

V Extension of MCTL to Full Length or to Recover Regulatory Elements

The nucleic acid sequence of full length mctl (SEQ ID NO:2) is used to design oligonucleotide primers for extending a partial nucleotide sequence to full length or for obtaining 5' sequences from genomic libraries. One primer is synthesized to initiate extension in the antisense direction (XLR) and the other is synthesized to extend sequence in the sense direction (XLF). Primers allow the extension of the known mctl sequence "outward" generating amplicons containing new, unknown nucleotide sequence for the region of interest (U.S. patent application Ser. No. 08/487,112, filed Jun. 7, 1995, specifically incorporated by reference). The initial primers are designed from the cDNA using OLIGO® 4.06 Primer Analysis Software (National Biosciences), or another appropriate program, to be 22–30 nucleotides in length, to have a GC content of 50% or more, and to anneal to the target sequence at temperatures about 68°–72° C. Any stretch of nucleotides which would result in hairpin structures and primer-primer dimerizations is avoided.

The original, selected cDNA libraries, or a human genomic library are used to extend the sequence; the latter is most useful to obtain 5' upstream regions. If more extension is necessary or desired, additional sets of primers are designed to further extend the known region.

By following the instructions for the XL-PCR kit (Perkin Elmer) and thoroughly mixing the enzyme and reaction mix, high fidelity amplification is obtained. Beginning with 40 pmol of each primer and the recommended concentrations of all other components of the kit, PCR is performed using the Peltier Thermal Cycler (PTC200; MJ Research, Watertown Mass.) and the following parameters:

| Step 1 | 94° C. for 1 min (initial denaturation) |
|--------|------------------------------------------|
| Step 2 | 65° C. for 1 min |
| Step 3 | 68° C. for 6 min |
| Step 4 | 94° C. for 15 sec |
| Step 5 | 65° C. for 1 min |

-continued

| Step 6 | 68° C. for 7 min |
| --- | --- |
| Step 7 | Repeat step 4–6 for 15 additional cycles |
| Step 8 | 94° C. for 15 sec |
| Step 9 | 65° C. for 1 min |
| Step 10 | 68° C. for 7:15 min |
| Step 11 | Repeat step 8–10 for 12 cycles |
| Step 12 | 72° C. for 8 min |
| Step 13 | 4° C. (and holding) |

A 5–10 μl aliquot of the reaction mixture is analyzed by electrophoresis on a low concentration (about 0.6–0.8%) agarose mini-gel to determine which reactions were successful in extending the sequence. Bands thought to contain the largest products were selected and cut out of the gel. Further purification involves using a commercial gel extraction method such as QIAQUICK™ (QIAGEN Inc). After recovery of the DNA, Klenow enzyme was used to trim single-stranded, nucleotide overhangs creating blunt ends which facilitate religation and cloning.

After ethanol precipitation, the products are redissolved in 13 μl of ligation buffer, 1 μl T4-DNA ligase (15 units) and 1 μl T4 polynucleotide kinase are added, and the mixture is incubated at room temperature for 2–3 hours or overnight at 16° C. Competent E. coli cells (in 40 μl of appropriate media) are transformed with 3 μl of ligation mixture and cultured in 80 μl of SOC medium (Sambrook J et al, supra). After incubation for one hour at 37° C., the whole transformation mixture is plated on Luria Bertani (LB)-agar (Sambrook J et al, supra) containing 2×Carb. The following day, several colonies are randomly picked from each plate and cultured in 150 μl of liquid LB/2μCarb medium placed in an individual well of an appropriate, commercially-available, sterile 96-well microtiter plate. The following day, 5 μl of each overnight culture is transferred into a non-sterile 96-well plate and after dilution 1:10 with water, 5 μl of each sample is transferred into a PCR array.

For PCR amplification, 18 μl of concentrated PCR reaction mix (3.3×) containing 4 units of rTth DNA polymerase, a vector primer and one or both of the gene specific primers used for the extension reaction are added to each well. Amplification is performed using the following conditions:

| Step 1 | 94° C. for 60 sec |
| --- | --- |
| Step 2 | 94° C. for 20 sec |
| Step 3 | 55° C. for 30 sec |
| Step 4 | 72° C. for 90 sec |
| Step 5 | Repeat steps 2–4 for an additional 29 cycles |
| Step 6 | 72° C. for 180 sec |
| Step 7 | 4° C. (and holding) |

Aliquots of the PCR reactions are run on agarose gels together with molecular weight markers. The sizes of the PCR products are compared to the original partial cDNAs, and appropriate clones are selected, ligated into plasmid and sequenced.

VI Labeling and Use of Hybridization Probes

Hybridization probes derived from SEQ ID NO:2 are employed to screen cDNAs, genomic DNAs or mRNAs. Although the labeling of oligonucleotides, consisting of about 20 base-pairs, is specifically described, essentially the same procedure is used with larger cDNA fragments. Oligonucleotides are designed using state-of-the-art software such as OLIGO 4.06 (National Biosciences), labeled by combining 50 pmol of each oligomer and 250 mCi of $[\gamma^{-32}P]$ adenosine triphosphate (Amersham, Chicago Ill.) and T4 polynucleotide kinase (DuPont NEN®, Boston Mass.). The labeled oligonucleotides are substantially purified with Sephadex G-25 super fine resin column (Pharmacia). A portion containing $10^7$ counts per minute of each of the sense and antisense oligonucleotides is used in a typical membrane based hybridization analysis of human genomic DNA digested with one of the following endonucleases (Ase I, Bgl II, Eco RI, Pst I, Xba 1, or Pvu II; DuPont NEN®)

The DNA from each digest is fractionated on a 0.7 percent agarose gel and transferred to nylon membranes (Nytran Plus, Schleicher & Schuell, Durham N.H.). Hybridization is carried out for 16 hours at 40° C. To remove nonspecific signals, blots are sequentially washed at room temperature under increasingly stringent conditions up to 0.1×saline sodium citrate and 0.5% sodium dodecyl sulfate. After XOMAT AR™ film (Kodak, Rochester N.Y.) is exposed to the blots in a Phosphoimager cassette (Molecular Dynamics, Sunnyvale Calif.) for several hours, hybridization patterns are compared visually.

VII Antisense Molecules

The mctl sequence, or any part thereof, is used to inhibit in vivo or in vitro expression of naturally occurring MCTL. Although use of antisense oligonucleotides, comprising about 20 base-pairs, is specifically described, essentially the same procedure is used with larger cDNA fragments. An oligonucleotide based on the coding sequence of MCTL as shown in FIGS. 1A, 1B and 1C is used to inhibit expression of naturally occurring MCTL. The complementary oligonucleotide is designed from the most unique 5' sequence as shown in FIGS. 1A and 1B and used either to inhibit transcription by preventing promoter binding to the upstream nontranslated sequence or translation of an mctl transcript by preventing the ribosome from binding. Using an appropriate portion of the leader and 5' sequence of SEQ ID NO:2, an effective antisense oligonucleotide includes any 15–20 nucleotides spanning the region which translates into the signal or early coding sequence of the polypeptide as shown in FIGS. 1A, 1B and 1C.

VIII Expression of MCTL Carbohydrate Binding Domain

Expression of the extracellular MCTL carbohydrate binding domain is accomplished by subcloning the cDNAs into appropriate vectors and transfecting the vectors into host cells. In this case, the cloning vector, PSPORT™, previously used for the generation of the cDNA library is used to express MCTL in E. coli. Upstream of the cloning site, this vector contains a promoter for β-galactosidase, followed by sequence containing the amino-terminal Met and the subsequent 7 residues of β-galactosidase. Immediately following these eight residues is a bacteriophage promoter useful for transcription and a linker containing a number of unique restriction sites.

Induction of an isolated, transfected bacterial strain with IPTG using standard methods produces a fusion protein which consists of the first seven residues of β-galactosidase, about 5 to 15 residues of linker, and the full length MCTL. The signal sequence directs the secretion of the MCTL carbohydrate binding domain into the bacterial growth media which can be used directly in the following assay for activity.

IX MCTL Activity

Lectin activity of MCTL or biologically active fragments thereof may be assayed by first labeling the MCTL protein or polypeptide with $^{125}$I Bolton-Hunter reagent (Bolton, AE and Hunter, WM (1973) Biochem J 133: 529). Candidate ligands (including polysaccharides, glycoproteins or whole cells) previously arrayed in the wells of a 96 well plate are incubated with the labeled MCTL, washed and any wells with labeled MCTL complex are assayed. Data obtained using different concentrations of MCTL are used to calculate values for the number, affinity, and association of MCTL with the candidate ligands.

X Production of MCTL Specific Antibodies

MCTL substantially purified using PAGE electrophoresis (Sambrook, supra) is used to immunize rabbits and to produce antibodies using standard protocols. The amino acid sequence translated from MCTL is analyzed using DNAS-TAR™ software (DNAStar Inc) to determine regions of high immunogenicity and a corresponding oligopolypeptide is synthesized and used to raise antibodies by means known to those of skill in the art. Analysis to select appropriate epitopes, such as those near the C-terminus or in hydrophilic regions (as shown in FIG. 3) is described by Ausubel FM et al (supra).

Typically, the oligopeptides are 15 residues in length, synthesized using an Applied Biosystems Peptide Synthesizer Model 431A using fmoc-chemistry, and coupled to keyhole limpet hemocyanin (KLH, Sigma) by reaction with M-maleimidobenzoyl-N-hydroxysuccinimide ester (MBS; Ausubel FM et al, supra). Rabbits are immunized with the oligopeptide-KLH complex in complete Freund's adjuvant. The resulting antisera are tested for antipeptide activity, for example, by binding the peptide to plastic, blocking with 1% BSA, reacting with rabbit antisera, washing, and reacting with radioiodinated, goat anti-rabbit IgG.

XI Purification of Naturally Occurring MCTL Using Specific Antibodies

Naturally occurring or recombinant MCTL is substantially purified by immunoaffinity chromatography using antibodies specific for MCTL. An immunoaffinity column is constructed by covalently coupling MCTL antibody to an activated chromatographic resin such as CnBr-activated Sepharose (Pharmacia Biotech). After the coupling, the resin is blocked and washed according to the manufacturer's instructions.

Cellular fractions from cells containing MCTL are prepared by solubilization of the whole cell and isolation of subcellular fractions by differential centrifugation, by the addition of detergent, or by other methods well known in the art. Alternatively, a soluble MCTL fragment containing a signal sequence may be secreted in useful quantitiy into the medium in which the cells are grown.

A fractionated MCTL-containing preparation is passed over the immunoaffinity column, and the column is washed under conditions that allow the preferential absorbance of MCTL (eg, high ionic strength buffers in the presence of detergent) The column is eluted under conditions that disrupt antibody/MCTL binding (eg, a buffer of pH 2–3 or a high concentration of a chaotrope such as urea or thiocyanate ion), and MCTL is collected.

All publications and patents mentioned in the above specification are herein incorporated by reference. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in molecular biology or related fields are intended to be within the scope of the following claims.

We claim:

1. A substantially purified polypeptide comprising the amino acid sequence of SEQ ID NO:1.

2. A substantially purified polypeptide comprising the amino acid sequence of SEQ ID NO:1 from about amino acid residue 66, threonine, to amino acid residue 201, methionine.

* * * * *